US007226941B2

(12) United States Patent
Park et al.

(10) Patent No.: US 7,226,941 B2
(45) Date of Patent: Jun. 5, 2007

(54) COMPOUND FOR TREATING ANGIOGENESIS

(75) Inventors: Jong Wan Park, Sung bok gu (KR); Yang-Gook Chun, Sung bok gu (KR); Kenneth Bair, Oakland, CA (US); Ho Sung Cho, San Diego, CA (US)

(73) Assignees: HIF Bio, Inc., Upland, CA (US); Bizbiotech Co., Ltd., Seoul (KR)

( * ) Notice: Subject to any disclaimer, the term of this patent is extended or adjusted under 35 U.S.C. 154(b) by 166 days.

(21) Appl. No.: 10/883,482

(22) Filed: Jun. 30, 2004

(65) Prior Publication Data

US 2005/0187276 A1  Aug. 25, 2005

Related U.S. Application Data

(60) Provisional application No. 60/484,158, filed on Jun. 30, 2003, provisional application No. 60/484,191, filed on Jun. 30, 2003, provisional application No. 60/534,001, filed on Dec. 31, 2003, provisional application No. 60/533,985, filed on Dec. 31, 2003.

(51) Int. Cl.
A61K 31/415 (2006.01)
C07D 231/54 (2006.01)

(52) U.S. Cl. .................................. 514/403; 548/360.1
(58) Field of Classification Search .................. None
See application file for complete search history.

(56) References Cited

U.S. PATENT DOCUMENTS

| 5,574,168 A * | 11/1996 | Kuo et al. ............... 548/360.5 |
| 6,162,819 A * | 12/2000 | Schindler et al. ........... 514/405 |
| 6,180,656 B1 * | 1/2001 | Robyr et al. ............... 514/406 |
| 6,387,940 B1 | 5/2002 | Straub et al. |
| 6,387,942 B2 | 5/2002 | Teng et al. .................. 514/414 |
| 6,410,740 B1 * | 6/2002 | Robyr et al. ................ 548/235 |
| 6,518,294 B2 | 2/2003 | Teng et al. .................. 514/403 |
| 6,589,997 B2 | 7/2003 | Pillarisetti et al. .......... 514/685 |
| 6,610,726 B2 | 8/2003 | Pillarisetti et al. .......... 514/406 |
| 6,897,232 B2 * | 5/2005 | Schindler et al. ........... 514/406 |
| 2003/0072748 A1 | 4/2003 | Black et al. |
| 2003/0105336 A1 | 6/2003 | Schindler et al. ........ 548/354.1 |
| 2003/0186996 A1 | 10/2003 | Teng et al. ............... 514/262.1 |
| 2004/0077702 A1 | 4/2004 | Fu et al. .................... 514/406 |

FOREIGN PATENT DOCUMENTS

| EP | 0254241 | 1/1988 |
| EP | 0667345 | 2/1995 |
| EP | 1166785 | 6/2001 |
| KR | 10-2001-0060054 | 9/2001 |
| WO | WO03/024397 | 3/2003 |
| WO | WO03/082274 | 10/2003 |
| WO | WO 2004/091648 A1 | 10/2004 |
| WO | WO 2005/030121 A2 | 4/2005 |

OTHER PUBLICATIONS

Chun, et al (Biochemical Pharmacology, 61 (Apr. 2001), 947-954), especially p. 947, compound YC-1, 3-(5'-hydroxymethyl-2'-furyl)-1-benzylindazole.*
Ko et al., "YC-1 a Novel Activator of Platelet Guanylate Cyclase", Blood, vol. 84, No. 12, Dec. 15, 1994, pp. 4226-4233.
Yeo et al., "YC-1: A Potential Anticancer Drug Targeting Hypoxia-Inducible Factor 1", Journal of the National Cancer Institute, vol. 95, No. 7, Apr. 2, 2003, pp. 516-525.
Höckel and Vaupel, "Tumor Hypoxia: Definitions and Current Clinical, Biologic, and Molecular Aspects", Journal of National Cancer Institute, vol. 93, No. 4, Feb. 21, 2001, pp. 266-276.
Dachs and Tozer, "Hypoxia Modulated Gene Expression: Angiogenesis, Metastasis, and Therapeutic Expoloitation", European Journal of Cancer, 36, May 2000, pp. 1649-1660.
J. Martin Brown, "The Hypoxic Cell: A Target for Selective Cancer Therapy", Eighteenth Bruce F. Cain Memorial Award Lecture, Cancer Research, 59, Dec. 1, 1999, pp. 5863-5870.
Forsythe et al., "Activation of Vascular Endothelial Growth Factor Gene Transcription by Hypoxia-Inducible Factor 1", Molecular and Cellular Biology, Sep. 1996, pp. 4604-4613.
Wang and Semenza, "Purification and Characterization of Hypoxia-Inducible Factor 1", The Journal of Biological Chemistry, vol. 270, No. 3, Jan. 20, 1995, pp. 1230-1237.
Maxwell et al., "The Tumour Suppressor Protein VHL Targets Hypoxia-Inducible Factors for Oxygen-Dependent Proteolysis," Nature, vol. 399, May 20, 1999, pp. 2710-2715.
Ivan et al., "HIFα Targeted for VHL-Mediated Destruction by Proline Hydroxylation: Implications for $O_2$ Sensing", Science, vol. 292, Apr. 20, 2001, pp. 464-451.
Masson et al., "Independent Function of Two Destruction Domains In Hypoxia-Inducible Factor-α Chains Activated by Polyl Hydroxylation," European Molecular Biology Organization, The EMBO Journal, vol. 20, No. 18, (2001) pp. 5197-5206.
Huang et al., "Regulation of Hypoxia-Inducible Factor 1α is Mediated by an O2-Dependent Degradation Domain Via the Ubiquitin-Proteasome Pathway," Proc. Natl. Acad. Sci USA, vol. 95, pp. 7987-7992, Jul. 1998.
Gregg L. Semenza, "HIF-1 and Tumor Progression: Pathophysiology and Therapeutics," Trends in Molecular Medicine, vol. 8, No. 4, Suppl. (2002), pp. S62-S67.
Zhong et al., "Overexpression of Hypoxia-Inducible Factor 1α in Common Human Cancers and Their Metastases", Cancer Research, vol. 59, pp. 5830-5835, Nov. 15, 1999.
Birner et al., "Overexpression of Hypoxia-Inducible Factor 1α Is a Marker For an Unfavorable Prognosis in Early-Stage Invasive Cervical Cancer", Cancer Research, vol. 60, pp. 4693-4696, Sep. 1, 2000.

(Continued)

Primary Examiner—Joseph K. McKane
Assistant Examiner—Susannah L. Chung
(74) Attorney, Agent, or Firm—JHK Law; Joseph Hyosuk Kim

(57) ABSTRACT

The present invention provides methods and pharmaceutical compositions for inhibiting expressions of HIF and HIF regulated genes, inhibiting angiogenesis, inducing cell cycle arrest in tumor cells, and treating cell proliferating diseases or conditions.

2 Claims, 23 Drawing Sheets

OTHER PUBLICATIONS

Maxwell et al., "Hypoxia-Inducible Factor-1 Modulated Gene Expression in Solid Tumors and Influences Both Angiogenesis and Tumor Growth", *Proc. Natl. Acad. Sci. USA*, vol. 94, pp. 8104-8109, Jul. 1997 Medical Sciences.

Teng et al., "YC-1 A Ntric Oxide-Independent Activator of Soluble Guanylate Cyclase, Inhibits Platelet-Rich Thrombosis in Mice", *European Journal of Pharmacology*, vol. 320, pp. 161-166, (1997).

Galle et al., "Effects of the Soluble Guanylyl Cyclase Activator, YC-1, on Vascular Tone, Cylcic GMP Levels and Phosphodiesterase Activity", *British Journal of Pharmacology*, vol. 127, pp. 195-203 (1999).

Chun et al., "Inhibitory Effect of YC-1 on the Hypoxic Induction of Erythropoietin and Vascular Endothelial Growth Factor in Hep3B Cells", *Biochemical Pharmacology*, vol. 61, pp. 947-954 (2001).

Yoshina et al., Yakugaku Zasshi, vol. 98(2), pp. 204-209, (1978).

Yoshina et al., Yakugaku Zasshi, vol. 97(9), pp. 955-961, (1977).

Jaakkola et al., "Targeting of HIF-$\alpha$ to the von Hippel—Lindau Ubiquitylation Complex by $O_2$-Regulated Prolyl Hydroxylation", Science, vol. 292, pp. 468-472, Apr. 20, 2001.

Giaccia et al., "HIF-1 As A Target For Drug Development", *Nature Reviews/Drug Discovery*, vol. 2, pp. 1-9, Oct. 2003.

Semenza, "Targeting HIF-1 For Cancer Therapy", *Nature Reviews/Cancer*, vol. 3, pp. 721-732, Oct. 2003.

* cited by examiner

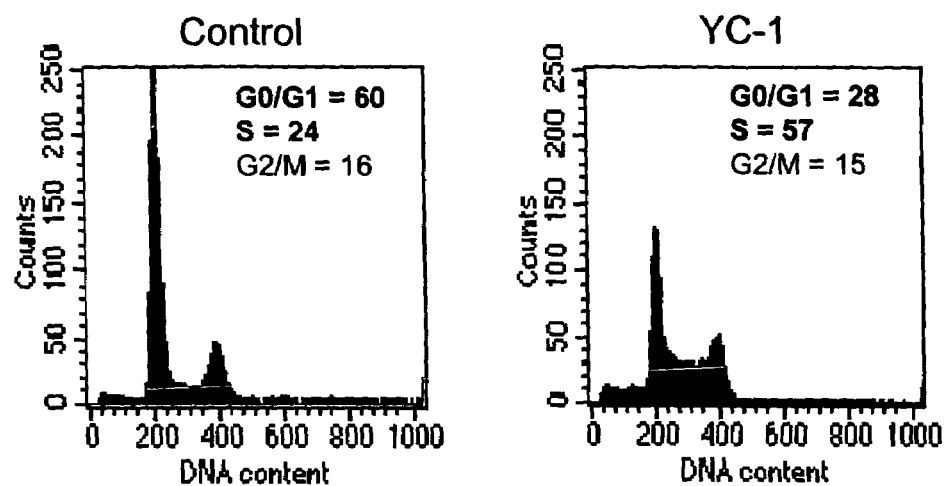
FIG. 1a
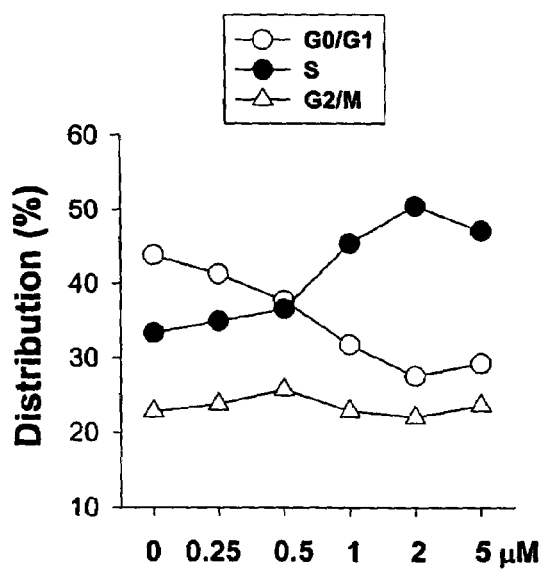
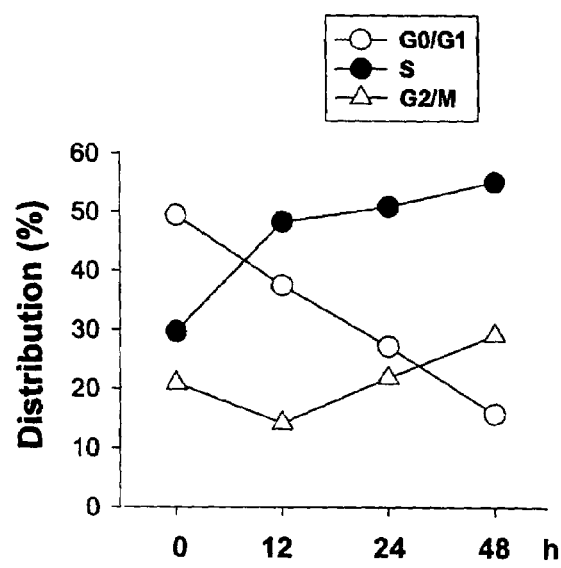
FIG. 1b  FIG. 1c

*In vitro* toxicity

*In vivo* acute toxicity

|   | 100 mg/kg | 200 mg/kg | 500 mg/kg |
|---|---|---|---|
| YC-1 | 0 | 0 | 30 |
| A | 0 | 0 | 0 |
| B | 0 | 0 | 60 |
| C | 0 | 0 | 16 |
| D | 0 | 0 | 100 |
| E | 0 | 0 | 40 |

Lethality = dead mice/total mice x 100%

FIG. 7

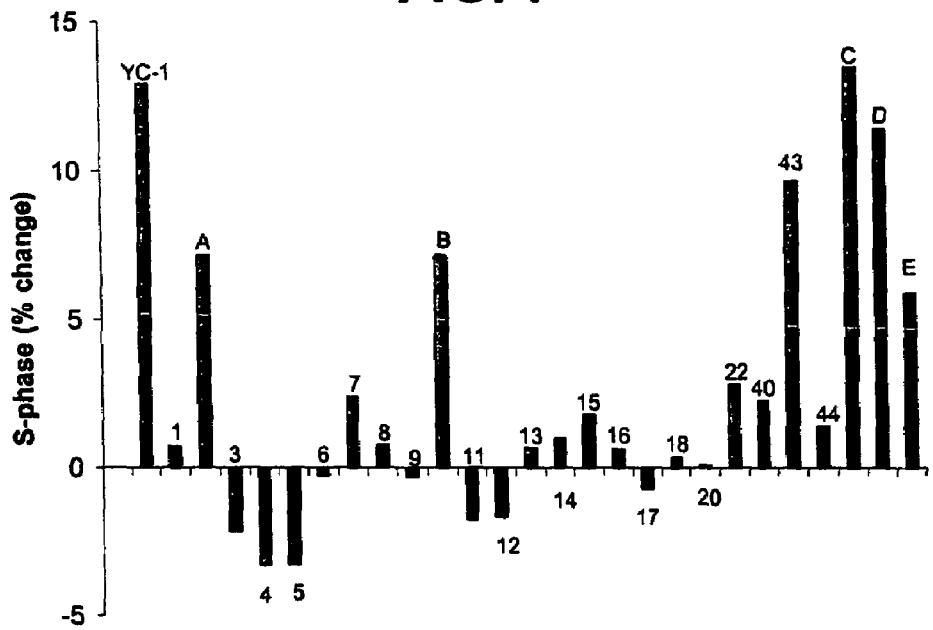

| | |
|---|---|
| 1 | [5-(1H-Indazol-3-yl)-furan-2-yl]-methanol |
| A | [5-(1-Methyl-1H-indazol-3-yl)-furan-2-yl]-methanol |
| 3 | [5-(1-Benzyl-1H-pyrazol-3-yl)-furan-2-yl]-methanol |
| 4 | 1-Benzyl-1H-indazole |
| 5 | 1-Benzyl-3-furan-2-yl-1H-indazole |
| 6 | 1-Benzyl-3-(5-methyl-furan-2-yl)-1H-indazole |
| 7 | (5-(1-benzyl-1H-indol-3-yl)furan-2-yl)methanol |
| 8 | (5-(1-benzylnaphthalen-4-yl)furan-2-yl)methanol |
| 9 | 1-Benzyl-3-(5-methoxymethyl-furan-2-yl)-1H-indazole |
| B | [5-(1-Benzyl-1H-indazol-3-yl)-1-methyl-1H-pyrrol-2-yl]-methanol |
| 11 | [6-(1-Benzyl-1H-indazol-3-yl)-pyridin-2-yl]-methanol |
| 12 | 2-[5-(1-Benzyl-1H-indazol-3-yl)-furan-2-yl]-propan-2-ol |
| 13 | [5-(1-Benzyl-1H-indazol-3-yl)-tetrahydro-furan-2-yl]-methanol |
| C | [5-(1-Thiophen-2-ylmethyl-1H-indazol-3-yl)-furan-2-yl]-methanol |
| 14 | (5-(2-((thiophen-2-yl)methyl)-2H-indazol-3-yl)furan-2-yl)methanol + C |
| 15 | [5-(1-Phenyl-1H-indazol-3-yl)-furan-2-yl]-methanol |
| 16 | [5-(1-Phenethyl-1H-indazol-3-yl)-furan-2-yl]-methanol |
| 17 | [5-(1-Cyclohexylmethyl-1H-indazol-3-yl)-furan-2-yl]-methanol |
| 18 | (2-(benzylamino)phenyl)(5-(hydroxymethyl)furan-2-yl)methanone |
| 20 | [3-(1-Benzyl-1H-indazol-3-yl)-phenyl]-methanol |
| 22 | 1-[5-(1-Benzyl-1H-indazol-3-yl)-furan-2-yl]-ethanol |
| 40 | {5-[1H-benzimidazol-1-yl]-furan-2-yl}-methanol |
| 43 | {5-[1-ethyl-1H-indazol-3-yl]-furan-2-yl}-methanol |
| 44 | {5-[1-(prop-2-yl)-1H-indazol-3-yl]-furan-2-yl}-methanol |
| D | (1-methyl-5-(1-methyl-1H-indazol-3-yl)-1H-pyrrol-2-yl)methanol |
| E | {N-methyl-5-[1-phenyl-1H-indazol-3-yl]-pyrrol-2-yl}-methanol |

COMPOUND FOR TREATING ANGIOGENESIS

CLAIM OF PRIORITY

The priority of provisional applications Ser. No. 60/484,158, filed Jun. 30, 2003, Ser. No. 60/484,191, filed Jun. 30, 2003, Ser. No. 60/534,001, filed Dec. 31, 2003 and Ser. No. 60/533,985, filed Dec. 31, 2003 is hereby claimed pursuant to 35 USC 119(e). The disclosures of these applications are incorporated by reference herein in their entirety.

FIELD OF THE INVENTION

The present invention relates to methods and pharmaceutical compositions for inhibiting tumor growth by arresting the cell cycle or by suppressing HIF-regulated gene expression, inhibiting angiogenesis in tumor cells or tissues, and for treating HIF mediated disorders or conditions.

BACKGROUND OF THE INVENTION

Hypoxia, a reduction in tissue oxygen levels below physiologic levels, commonly develops within solid tumors because tumor cell proliferation is greater than the rate of blood vessel formation. Thus, the increase in tumor mass results in aberrant vasculature formation, which compromises the blood supply (Hockel et al., J Natl Cancer Inst 2001 93:266-276). Tumor hypoxia is one stimulus that leads to the increased expression of vascular endothelial growth factor (VEGF) and stimulates angiogenesis, which is essential for meeting the metabolic requirements of tumor growth (Dachs et al., Eur J Cancer 2000 36:1649-1660). In addition, hypoxia contributes to tumor progression to a more malignant phenotype because cells surviving under hypoxic conditions often become resistant to radiotherapy and chemotherapy (Brown, J. M. Cancer Res 1999 59:5863-5870). Thus, factors that regulate the hypoxic events may be good targets for anticancer therapy.

One such target is hypoxia-inducible factor 1 (HIF-1). HIF-1 is a key transcription factor that regulates the blood supply through the expression of vascular endothelial growth factor (VEGF) (Forsythe et al., Mol Cell Biol 1996 16:4604-4613). The biologic activity of HIF-1, a heterodimer composed of HIF-1α and HIF-1β (Wang et al., J Biol Chem 1995 270:1230-1237), depends on the amount of HIF-1α, which is tightly regulated by oxygen tension. Under normoxic conditions, HIF-1α protein is unstable. The instability is mainly regulated by the binding to the von Hippel-Lindau tumor suppressor protein (pVHL) (Maxwell et al., Nature 1999 399:271-275). This binding occurs after the hydroxylation of the two HIF-1α proline residues by HIF-prolyl hyroxylases (Jaakkola et al., Science 2001 292:468-472; Ivan et al., Science 2001 292:464-468; Masson et al., EMBO J. 2001 20:5197-5206). The von Hippel-Lindau protein is one of the components of the multiprotein ubiquitin-E3-ligase complex, which mediates the ubiquitylation of HIF-1α, targeting it for proteasomal proteolysis (Huang et al., Proc Natl Acad Sci USA 1998 95:7987-7992). However, under hypoxic conditions, proline hydroxylation is inhibited, binding between HIF-1 and the von Hippel-Lindau protein is eliminated and HIF-1α becomes stable.

HIF-2α (also known as endothelial PAS protein-1 or MOP2) is another member in HIF family. It was found by homology searches in the gene bank and by cloning experiments. HIF-2α is highly similar to HIF-1α in protein structure, but exhibits restricted tissue-specific expression. HIF-2α is also tightly regulated by oxygen tension and its complex with HIF-1β appears to be directly involved in hypoxic gene regulation, as is HIF-1α. Since HIF-2α is expressed in a number of cancer cell lines and involved in hypoxic gene regulation, HIF-2α is also suggested to be associated with tumor promotion, but may not contribute to the growth of most tumors. In breast cancer cell lines that express both HIF-1α and HIF-2α, HIF-1α rather than HIF-2α appears to predominantly contribute to the transcriptional response to hypoxia. However, HIF-2α may take over the role of HIF-1α in tumors that express only HIF-2α. Indeed, in von Hippel-Lindau (VHL)-defective 786-O renal cell carcinoma cells, the transcriptional response to hypoxia depended on expression levels of HIF-2α. Moreover, the ectopic expression of HIF-2α led to enhanced growth of 786-O tumors grafted in nude mice. Therefore, HIF-2α is also a good target for cancer treatment. See Semenza, G. L., Nature Reviews, Cancer, Vol. 3, (2003), pp. 70-81.

As used herein, the term HIF means the combined effect of or total proteins of HIF-1 plus HIF-2. In addition the term HIF-1 means the combined effect of or total proteins of HIF-1α plus HIF-1β. The term HIF-2 means the combined effect of or total proteins of HIF-2α plus HIF-2β.

While searching for anticancer agents that inhibit HIF-1 activity, we identified a novel pharmacologic action of YC-1 and novel analogs thereof. YC-1, 3-(5'-hydroxymethyl-2'-furyl)-1-benzylindazole, has been known to inhibit platelet aggregation and vascular contraction by activating soluble guanylyl cyclase, and was originally developed as a potential therapeutic agent for circulation disorders (Teng et al., Eur J Pharmacol 1997 320:161-166; Galle et al., Br J Pharmacol 1999 127:195-203). Recently, we have found two novel biological actions of YC-1 and novel analogs thereof; one is the inhibitory effect on either HIF-1 or HIF-2 activity, and the other is the anti-proliferative effect on cancer cells by arresting the cell cycle and leading to cell apoptosis.

The inhibitory effects of compounds of the invention on the expression of HIF-1α and on the induction of VEGF, aldolase A, and enolase I in cancer cells cultured under hypoxic conditions are also exhibited in vivo, treatment by halting the growth of xenografted tumors originating from human cancers, such as hepatoma, stomach carcinoma, renal carcinoma, cervical carcinoma, neuroblastoma, and prostate carcinoma cells. Tumors from mice treated with the compounds showed fewer blood vessels and reduced expression of HIF-1α protein and HIF-1-regulated genes than tumors from vehicle-treated mice. These results support that the compounds are inhibitors of HIF-1 and HIF-2, and halt tumor growth by blocking tumor angiogenesis and tumor adaptation to hypoxia. The compounds are also useful against tumors that overexpress HIF proteins.

The eukaryotic cell cycle is divided into four stages: G1, S, G2, and M. G1 is the gap phase during which cells prepare for the process of DNA replication. During this phase, cells integrate mitogenic and growth-inhibitory signals and make the decision to proceed, pause, or exit cell cycle. The S Phase is defined as the stage in which DNA synthesis occurs. G2 is the second gap phase during which the cell prepares for the process of division. The M phase is defined as the stage in which the replicated chromosomes are segregated into separate nuclei and other cellular components are divided to make two daughter cells. In addition to G1, S, G2, and M, G0 is defined as the cell stage in which cells exit cell cycle and become quiescent. Cells have evolved signaling pathways to coordinate cell cycle transitions and ensure faithful replication of the genome before cell division. Cell cycle progression is stimulated by protein kinase complexes, each of which consists of a cyclin and a cyclin-dependent kinase (CDK). The CDK's are expressed constitutively through cell cycle, whereas cyclin levels are restricted by transcriptional regulation of the cyclin genes and by ubiquitin-mediated degradation. The CDK activation requires the binding of a cyclin partner in addition to site-specific phosphorylation. To carry on error-free cell cycle, eukaryotic cells have developed control mechanisms that restrain cell cycle transitions in response to stress. These regulatory pathways are termed cell cycle checkpoints, which can be divided into three points, i.e., G1-S, G2, and M phase checkpoint. Cells can arrest transiently at cell cycle checkpoints to allow for the repair of cellular damage. Alternatively, when the cell cycle arrest is due to irreparable damage, checkpoint signaling activates pathways that lead to apoptosis.

In most proliferative disorders, such as benign/malignant tumors, various visceral hyperplasia, vascular wall thickening due to smooth muscle cell proliferation, psoriasis and proliferative retinal diseases, limitless cell proliferation is the most important manifestation. Basically, these disorders are caused by cell cycle dysregulation. Several genes encoding regulatory proteins that govern cell cycle are targets for genetic and epigenetic alterations that underlie the genesis of the proliferative disorders. The best characterized of these genes are D-type cyclins. Amplification of the cyclin D genes occurs in a subset of breast, esophageal, bladder, lung, and squamous cell carcinomas. In addition, cyclin D proteins are over-expressed in some primary tumors and other proliferative disorders. In addition, the catalytic partners of D-type cyclins cdk4 and cdk6 are over-expressed and hyperactivated in some tumors and tumor cell lines. Alterations in other cell cycle regulators have also been implicated in human cancer. Cyclin E has been found to be amplifed, overexpressed, or both in some breast, colon carcinomas, and leukemias. A single instance in which cyclin A was altered in a human hepatoma has been reported. Besides these cell cycle regulators, the genetic alterations of the checkpoint regulators that induce cell cycle arrest are also associated with the genesis of the proliferative disorders.

The p53 gene, whose product plays a key role in checkpoint regulation of cell cycle, is the most frequently mutated gene in human cancer. The stabilization of p53 in response to DNA damage results in enhanced expression of p21, which in turn stops cell cycle at the G1 and G2 phases. This cell cycle arrest makes damaged cells take the time for DNA repair. However, if the DNA damage is irreparable, p53 induces cell death by activating the apoptotic process, which is independent of p21.

Since the disruption of normal cell cycle regulation is the hallmark of cancer, there are numerous opportunities for targeting checkpoint controls to develop new therapeutic strategies for this disease. Such strategies include induction of checkpoint arrest leading to cytostasis and ultimately apoptosis, arrest of proliferating cells in stages of the cell cycle which may sensitize them to treatment with other therapeutic agents such as radiation, and targeting of therapies toward specific regulatory components of the cell cycle. Most anticancer agents intervene at multiple points in the cell cycle. They have diverse mechanisms of action and exhibit specificity in terms of the stage of the cell cycle in which they target i.e., DNA damaging anticancer agents lead to G1/S or G2/M arrest; microtubule targeting agents lead to M arrest; antimetabolites lead to S arrest; and topoisomerase inhibitors lead to S or G2/M arrest. In addition, some potentially successful therapeutic strategies involve the use of agents that target cell cycle regulatory molecules. Chemical inhibitors of cdks, which exhibit specificity for cdk1 and cdk2, can induce both G1 and G2 arrest as well as apoptosis. Therefore, chemicals that specifically cause cell cycle arrest may be useful therapeutic agents for treating cancers and other proliferating disorders irrespective of their target molecules.

The compounds of the invention are also useful for treating non-cancer diseases or conditions which are HIF-mediated or VEGF-mediated. Such diseases or conditions include: atherosclerosis, (Couffinhal et al. Am J Pathol 1997 150:1673-1685); diabetic retinopathy, (Boulton et al. Br J Ophthalmol 1998 82:561-568); cardiac hypertophy, (Kakinuma et al., Circulation 2001 103:2387-23945); vacular remodeling, (Semnza G L, Respir Res 2000 1:159-162); pulmonary hypertension, (Semnza G L, Respir Res 2000 1:159-162); pre-eclampsia, (Caniggia et al., Placenta 2000 21: S25-S30); arthritis, (Anthony et al., Arthritis and Rheumatism 2001 44: 1540-1544); inflammatory disease, (Cramer et al., Cell 2003 112: 645-657); and psoriasis (Bhushan et al., Br. J. Dermatol 1999 141: 1054-1060).

Thus, compounds according to the present invention are useful therapeutic agents, as single agents or when combined with other anticancer therapies, for treating tumors and other proliferative disorders, such as hyper-proliferative skin orders, via inhibition of cell cycle progression.

DESCRIPTION OF THE FIGURES

FIG. 1 shows the S-phase arrest induced by YC-1 treatment in Hep3B hepatoma cells. FIG. 1a is the FACS data to analyze the cell distribution based on DNA content. FIG. 1b is a dose-response curve for the effect of 24 h YC-1 treatment on cell cycle. FIG. 1c is a time course for the effect of 1 µM YC-1 on cell cycle. The cell cycle analysis was performed using a Becton Dickinson FACStar flow cytometer. Cells ($1-2\times10^6$) were plated in 10 cm culture dishes at concentrations determined to yield 70-80% confluence within 24 h. Cells were treated with DMSO or YC-1 and incubated for described time. After incubation, both adherent and floating cells were harvested, washed with 3 ml PBS and resuspended with 200 µl PBS, fixed in 75% ethanol for 30 min on ice. After washing with PBS, cells were labeled with propidium iodide (0.05 mg/ml) in the presence of RNase A (0.5 mg/ml), incubated at room temperature in the dark for 30 min. DNA content was then analyzed using FACStar flow cytometer, and then excited with an argon, water-cooled laser emitting at 488 nm. Propidium iodide was detected using a $630\pm20$ nm band pass filter.

FIG. 3 is the apoptotic effect of YC-1.

Caspase-3 is an enzyme that digests the 113 kDa protein poly-ADP-ribose-polymerase (PARP) to form an inactive 89 kDa fragment. PARP is essential for DNA-replication in the S-phase and its absence leads to apoptosis.

FIG. 4a is the assay for comparison using YC-1.

FIG. 7 is a plot summarizing the effects of some compounds according to the invention on induced S-phase arrest of the cell cycle. The Y-axis represents the difference in S-phase population compared to the control (% S-phase of test compound minus % S-phase of the control).

SUMMARY OF THE INVENTION

Figure 2:
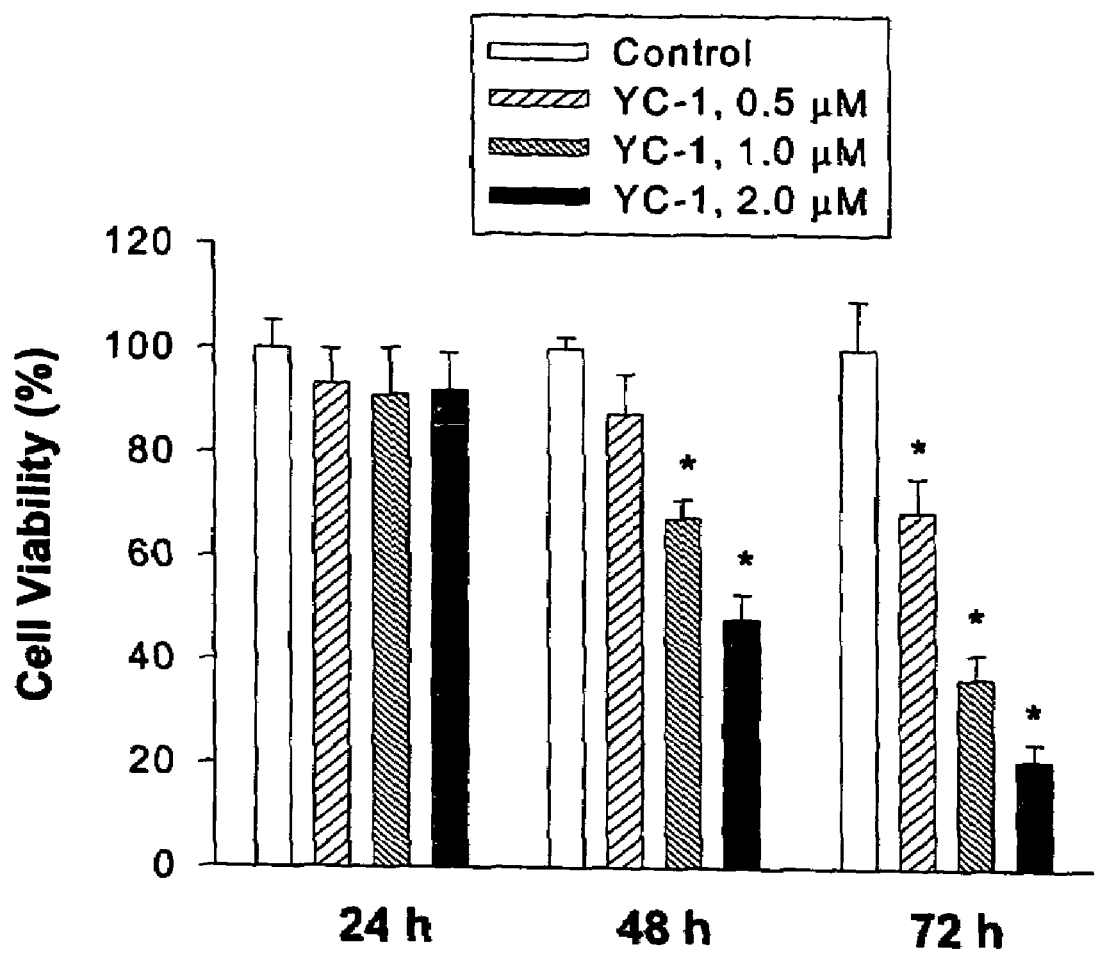
FIG. 2 shows cell death effect of YC-1 on Hep3B cells. The percentages of viable cells were measured by MTT assay. Cells were incubated with the indicated concentration of YC-1 for indicated time. Bars represent the mean of three separate experiments with the upper 95% confidence interval. *: $p<0.05$ vs. the control.

The present invention relates to anti-tumor treatment and treatment of other proliferative disorders or conditions by administration of a cell cycle arresting compound. In a particular aspect of the present invention the compounds are of Formula I:

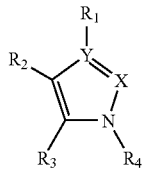

wherein:
X is N or $CR_6$; Y is N or C;
$R_1$ is optionally substituted alkyl, optionally substituted aryl, or optionally substituted heterocyclyl; or $R_1$ is absent if Y is N;
$R_2$ and $R_3$ are independently chosen from hydrogen or optionally substituted alkyl; or $R_2$ and $R_3$, together with the carbons to which they are attached form an optionally substituted aromatic or optionally substituted heteroaromatic ring; and
$R_4$ is optionally substituted aryl, optionally substituted heterocyclyl, or optionally substituted alkyl;
$R_6$ is hydrogen, optionally substituted aryl, optionally substituted heterocyclyl, or optionally substituted alkyl;
including single isomers, mixtures of isomers, and pharmaceutically acceptable solvates and salts thereof;

In a particular aspect of the present invention, the compounds are of Formula II:

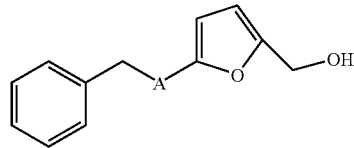

wherein:
A is —NH—$R_5$—(CO)—, —(CO)—$R_5$—NH— or naphthyl; and
$R_5$ is optionally substituted phenyl or optionally substituted pyridinyl.

Methods and pharmaceutical compositions for administering compounds of Formula I or II to animals to inhibit tumor progression or treat other proliferative disorders are also provided. The invention also provides methods and pharmaceutical compositions for combining compounds of Formula I or II with other anticancer agents or therapies. Compounds of the Formula III are also provided. Formula III

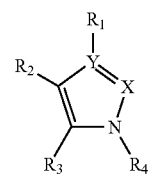

wherein
X is N, or $CR_6$; Y is N or C;
$R_1$ is optionally substituted heterocyclyl, provided that when Y=N, and X=CH, $R_1$ is absent;
$R_4$ is aryl of 5 to 14 carbon atoms or alkyl of 1-10 carbon atoms;
except that when Y=N and X=CH, $R_4$ may be optionally substituted heterocyclyl;
$R_6$ is hydrogen, optionally substituted aryl, optionally substituted heterocyclyl, or optionally substituted alkyl;
and $R_2$ and $R_3$ are independently hydrogen, optionally substituted alkyl, or $R_2$ and $R_3$ together with the carbon atoms to which they are attached form an optionally substituted aryl or optionally substituted heteroaryl ring.

DETAILED DESCRIPTION OF THE INVENTION

Definitions

As used in the present specification, the following words and phrases are generally intended to have the meanings as set forth below, except to the extent that the context in which they are used indicates otherwise.

"Alkyl" is intended to include linear, branched, or cyclic hydrocarbon structures and combinations thereof. Lower alkyl refers to alkyl groups of from 1 to 5 carbon atoms. Examples of lower alkyl groups include methyl, ethyl, propyl, i-propyl, butyl, s- and t-butyl and the like. Preferred alkyl groups are those of $C_{20}$ or below. More preferred alkyl groups are those of $C_{13}$ or below. Still more preferred alkyl groups are those of $C_6$ and below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene is another subset of alkyl, referring to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include n-butyl, s-butyl, i-butyl and t-butyl; "propyl" includes n-propyl and i-propyl.

The term "alkoxy" or "alkoxyl" refers to the group —O-alkyl, preferably including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

The term "substituted alkoxy" refers to the group —O-(substituted alkyl). One preferred substituted alkoxy group is "polyalkoxy" or —O-(optionally substituted alkylene)-(optionally substituted alkoxy), and includes groups such as —$OCH_2CH_2OCH_3$, and glycol ethers such as polyethyleneglycol and —$O(CH_2CH_2O)_xCH_3$, where x is an integer of about 2-20, preferably about 2-10, and more preferably about 2-5. Another preferred substituted alkoxy group is hydroxyalkoxy or —$OCH_2(CH_2)_yOH$, where y is an integer of about 1-10, preferably about 1-4.

"Acyl" refers to groups of from 1 to 10 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, i-butyryl, t-butoxycarbonyl, benzyloxycarbonyl and the like. "Lower-acyl" refers to groups containing 1 to 4 carbons and "acyloxy" refers to the group O-acyl.

The term "amino" refers to the group —$NH_2$. The term "substituted amino" refers to the group —NHR or —NRR where each R is independently selected from the group: optionally substituted alkyl, optionally substituted alkoxy, optionally substituted amino, optionally substituted aryl, optionally substituted heteroaryl, optionally substituted heterocyclyl, acyl, alkoxycarbonyl, sulfanyl, sulfinyl and sulfonyl, e.g., diethylamino, methylsulfonylamino, furanyl-oxy-sulfonamino.

"Aryl" and "heteroaryl" mean a 5-, 6- or 7-membered aromatic or heteroaromatic ring containing 0-4 heteroatoms selected from O, N or S; a bicyclic 9- or 10-membered aromatic or heteroaromatic ring system containing 0-4 (or more) heteroatoms selected from O, N or S; or a tricyclic 12- to 14-membered aromatic or heteroaromatic ring system containing 0-4 (or more) heteroatoms selected from O, N or S. The aromatic 6- to 14-membered aromatic carbocyclic rings include, e.g., phenyl, naphthalene, indane, tetralin, and fluorene and the 5- to 10-membered aromatic heterocyclic rings include, e.g., imidazole, oxazole, isoxazole, oxadiazole, pyridine, indole, thiophene, benzopyranone, thiazole, furan, benzimidazole, quinoline, isoquinoline, quinoxaline, pyrimidine, pyrazine, tetrazole and pyrazole.

"Aralkyl" refers to a residue in which an aryl moiety is attached to the parent structure via an alkyl residue. Examples include benzyl, phenethyl, phenylvinyl, phenylallyl and the like. "Heteroaralkyl" refers to a residue in which a heteroaryl moiety is attached to the parent structure via an alkyl residue. Examples include furanylmethyl, pyridinylmethyl, pyrimidinylethyl and the like.

"Halogen" or "halo" refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heterocycle" means a cycloalkyl or aryl residue in which one to four of the carbons is replaced by a heteroatom such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, oxadiazole, dioxane, tetrahydro furan and the like. "N-heterocyclyl" refers to a nitrogen-containing heterocycle as a substituent residue. The term heterocyclyl encompasses heteroaryl, which is a subset of heterocyclyl. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

"Substituted-" alkyl, aryl, heteroaryl and heterocyclyl refer respectively to alkyl, aryl, heteroaryl and heterocyclyl wherein one or more (up to about 5, preferably up to about 3) hydrogen atoms are replaced by a substituent independently selected from the group: optionally substituted alkyl (e.g., fluoroalkyl), optionally substituted alkoxy, alkylenedioxy (e.g. methylenedioxy), optionally substituted amino (e.g., alkylamino and dialkylamino), optionally substituted amidino, optionally substituted aryl (e.g., phenyl), optionally substituted aralkyl (e.g., benzyl), optionally substituted aryloxy (e.g., phenoxy), optionally substituted aralkoxy (e.g., benzyloxy), carboxy (—COOH), carboalkoxy (i.e., acyloxy or —OOCR), carboxyalkyl (i.e., esters or —COOR), carboxamido, aminocarbonyl, benzyloxycarbonylamino (CBZ-amino), cyano, carbonyl, halogen, hydroxy, optionally substituted heteroaryl, optionally substituted heteroaralkyl, optionally substituted heteroaryloxy, optionally substituted heteroaralkoxy, nitro, sulfanyl, sulfinyl, sulfonyl, and thio.

The term "sulfanyl" refers to the groups: —S-(optionally substituted alkyl), —S-(optionally substituted aryl), —S-(optionally substituted heteroaryl), and —S-(optionally substituted heterocyclyl).

The term "sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocyclyl).

The term "sulfonyl" refers to the groups: —$S(O_2)$—H, —$S(O_2)$-(optionally substituted alkyl), —$S(O_2)$-(optionally substituted amino), —$S(O_2)$-(optionally substituted aryl), —$S(O_2)$-(optionally substituted heteroaryl), —$S(O_2)$-(optionally substituted heterocyclyl), —$S(O_2)$-(optionally substituted alkoxy), —$S(O_2)$-optionally substituted aryloxy), —$S(O_2)$-(optionally substituted heteroaryloxy), and —$S(O_2)$-(optionally substituted heterocyclyloxy).

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical, synthetically nonfeasible and/or inherently unstable.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)—isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, or other organic acids known to be useful for creation of phamaceutically acceptable acid addition salts. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as i-propylamine, trimethylamine, diethylamine, triethylamine, tripropylamine, and ethanolamine.

The term "therapeutically effective amount" or "effective amount" refers to that amount of a compound of Formula I or II that is sufficient to effect treatment, as defined below, when administered alone or in combination with other anticancer therapies to a mammal in need of such treatment. More specifically, it is that amount that is sufficient to inhibit expression of HIF regulated genes or to induce cell cycle arrest. This, at the tumor site will inhibit tumor growth, tumor progression and metastasis without adverse side effects. As used herein, "HIF-related genes" as used herein refer to the genes whose expressions are regulated by HIF. The following genes are included in this gene family; erythropoietin, transferrin, transferrin receptor, ceruloplasmin, vascular endothelial growth factor (VEGF), VEGF receptor FLT-1, transforming growth factor β3, plasminogen activator inhibitor 1, α1B adrenergic receptor, adrenomedullin, endothelin 1, nitric oxide synthase 2, heme oxygenase 1, glucose transporter 1 & 3, hexokinase 1 & 2, enolase 1, glyceraldehyde-3-phosphate dehydrogenase, phosphoglycerate kinase 1, phosphoglucokinase L, pyruvate kinase M, aldolase A & C, trios phosphate isomerase, lactate dehydrogenase A, carbonic anhydrase 9, adenylate kinase 3, prolyl-4-hydroxylase a1, insulin-like growth factor (IGF) 2, IGF-binding protein 1, 2 & 3, P21, Nip3, cyclin G2 and differentiated embryo chondrocyte 1, The term "animal" as used herein is meant to include all mammals, and in particular humans. Such animals are also referred to herein as subjects or patients in need of treatment. The therapeutically effective amount will vary depending upon the subject and disease condition being treated, the weight and age of the subject, the severity of the disease condition, the particular compound of Formula I or II chosen, the dosing regimen to be followed, timing of administration, the manner of administration and the like, all of which can readily be determined by one of ordinary skill in the art.

The term "treatment" or "treating" means any treatment of a disease in a mammal, including:

a) preventing the disease, that is, causing the clinical symptoms of the disease not to develop;

b) inhibiting the disease, that is, slowing or arresting the development of clinical symptoms; and/or c) relieving the disease, that is, causing the regression of clinical symptoms.

Compounds of the Present Invention

The present invention is directed to the compounds represented by Formula I or II, which are selective to inhibit angiogenesis, and the expressions of HIF-1α, HIF-2α, and the HIF-regulated genes in vitro and in vivo to induce cell cycle arrest, as follows:

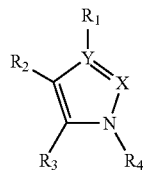

Formula I wherein:
X is N or $CR_6$; Y is N or C;
$R_1$ is optionally substituted alkyl, optionally substituted aryl, or optionally substituted heterocyclyl; or $R_1$ is absent if Y is N;
$R_2$ and $R_3$ are independently chosen from hydrogen or optionally substituted alkyl; or $R_2$ and $R_3$, together with the carbons to which they are attached form an optionally substituted aromatic or optionally substituted heteroaromatic ring; and
$R_4$ is optionally substituted aryl, optionally substituted heterocyclyl, or optionally substituted alkyl;
$R_6$ is hydrogen, optionally substituted aryl, optionally substituted heterocyclyl, or optionally substituted alkyl;
including single isomers, mixtures of isomers, and pharmaceutically acceptable solvates and salts thereof; or

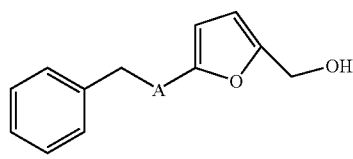

wherein:
A is —NH—$R_5$—(CO)—, —(CO)—$R_5$—NH— or naphthyl; and
$R_5$ is optionally substituted phenyl or optionally substituted pyridinyl, including single isomers, mixtures of isomers, and pharmaceutically acceptable solvates and salts thereof.
Compounds of the Formula III are also provided. Formula III

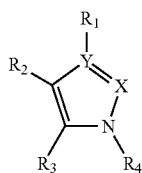

wherein
X is N, or $CR_6$; Y is N or C;
$R_1$ is optionally substituted heterocyclyl, provided that when Y=N, and X=CH, $R_1$ is absent;
$R_4$ is aryl of 5 to 14 carbon atoms or alkyl of 1-10 carbon atoms;

except that when Y=N and X=CH, $R_4$ may be optionally substituted heterocyclyl;
$R_6$ is hydrogen, optionally substituted aryl, optionally substituted heterocyclyl, or optionally substituted alkyl;
and $R_2$ and $R_3$ are independently hydrogen, optionally substituted alkyl, or $R_2$ and $R_3$ together with the carbon atoms to which they are attached form an optionally substituted aryl or optionally substituted heteroaryl ring.

Nomenclature

The compounds of Formula I and II can be named and numbered (e.g., using AutoNom version 2.1) as described below. For example, the compound of Formula IA:

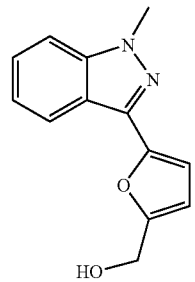

Formula IA i.e., the compound according to Formula I where $R_1$ is hydroxymethylfuranyl-; $R_2$ and $R_3$ together with the carbons to which they are attached form a fused benzo group; and $R_4$ is methyl, can be named [5-(1-methyl-1H-indazol-3-yl)-furan-2-yl]-methanol.

Synthesis of the Compounds of Formula I and II

The compounds of the invention can be synthesized utilizing techniques well known in the art from commercially available starting materials. See, e.g., U.S. Pat. Nos. 6,162,819; 6,518,294; and 5,574,168 and European Patent Application No. 254, 241, each of which is incorporated herein by reference in its entirety.

Benzimidazole derivatives may be synthesized by substitution on a suitable benzimidazole starting material with an appropriate alkyl, aryl or heteroaryl-halide. Useful reaction conditions include carrying out the condensation in the presence of cuprous iodide, a weak base, such as N,N'-dimethyl-ethylenediamine, and cesium carbonate.

YC-1, 3-(5'-hydroxymethyl-2'-furyl)-1-benzylindazole, a comparison compound to compounds of the present invention, may be manufactured by prior art techniques or is also available commercially. For example, YC-1 may be obtained from A.G. Scientific Inc. (San Diego, Calif.), Sigma RBI (St Louis, Mo., USA), or Alexis Biochemicals (San Diego, Calif.).

Figure 8:
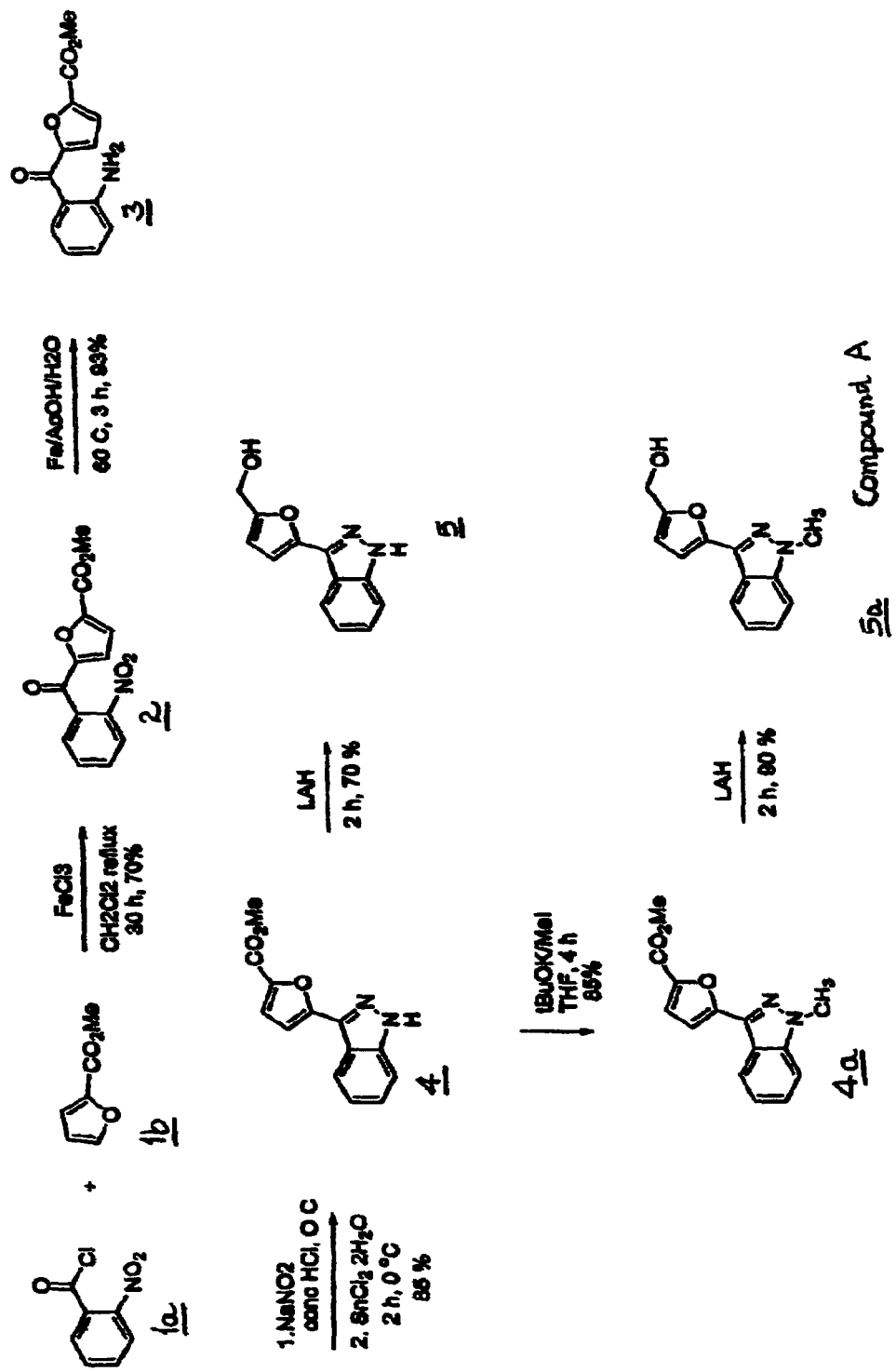
FIGS. 8 through 17 are synthetic schemes for making compounds according to the invention.

In addition, some of the compounds of the invention may be synthesized with reference to syntheses schematically shown in the figures. Referring to FIG. 8 there is shown a scheme for generally making 1-alkyl and 1-aryl substituted indazoles, such as compounds identified as 5 and 5a. Condensation of 1a and 1b produces the nitro ketone 2, which is selectively reduced to amino ketone 3. Nitration and reduction produce the cyclic product 4 that is then either reduced to form 5 or alkylated (or arylated) to form 5a. The compound 5a is also identified as Compound A herein.

Figure 9:
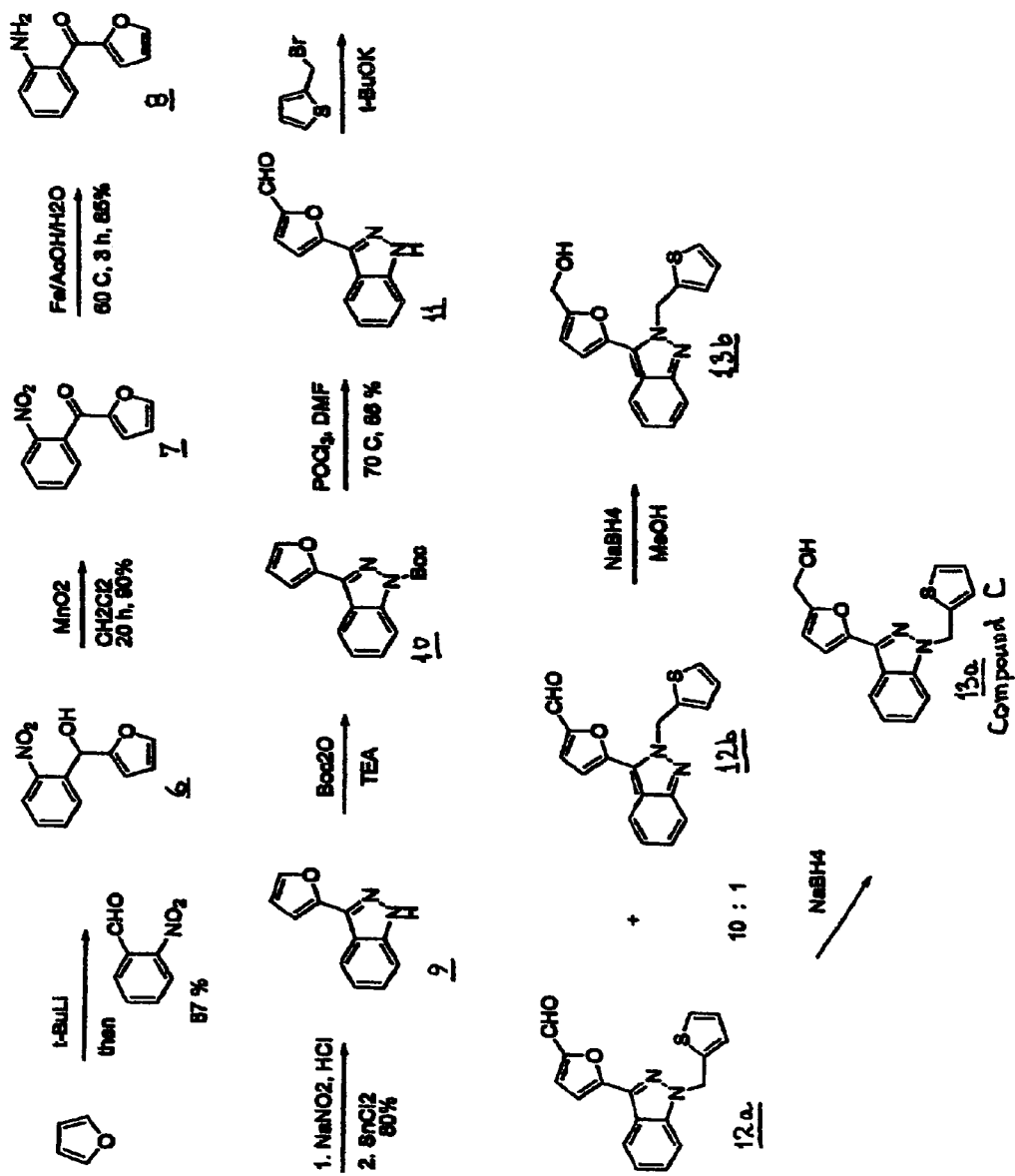

Referring to FIG. 9 there is shown a scheme for making 1- or 2-substituted indazoles. Condensation of furan and an appropriately substituted benzaldehyde leads to 6. Selective oxidation, reduction, nitration and cyclization sequentially produce 7, 8 and 9. After N-protection, carbonylation and deprotection, the indazole 11 is alkylated at the 1- and 2-positions, the isomers separated and reduced to produce 13a and 13b. Compound 13a is also identified as Compound C herein.

Figure 10:
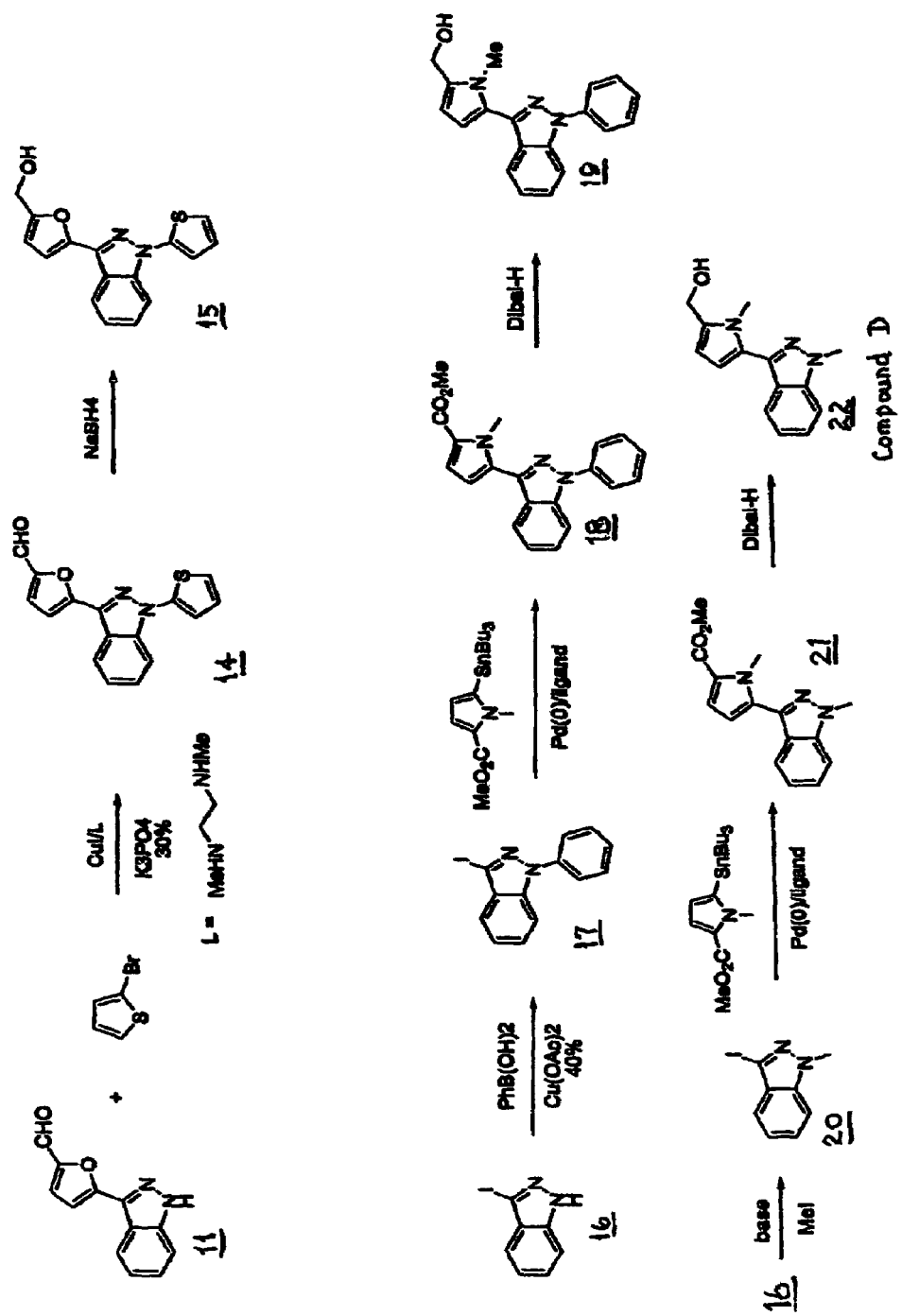

Referring to FIG. 10, there are shown schemes for making 1-aryl and 1-alkyl indazoles. Intermediate 11, described above is arylated and reduced to produce the 1-thienyl indazole 15. 3-iodo-indazole 16 is selectively arylated at the 1- and 3-positions, then reduced to produce the 1-phenyl indazole 19. The 1-methyl indazole 22 is similarly produced. Compound 22 is also identified as Compound D herein.

Figure 11:
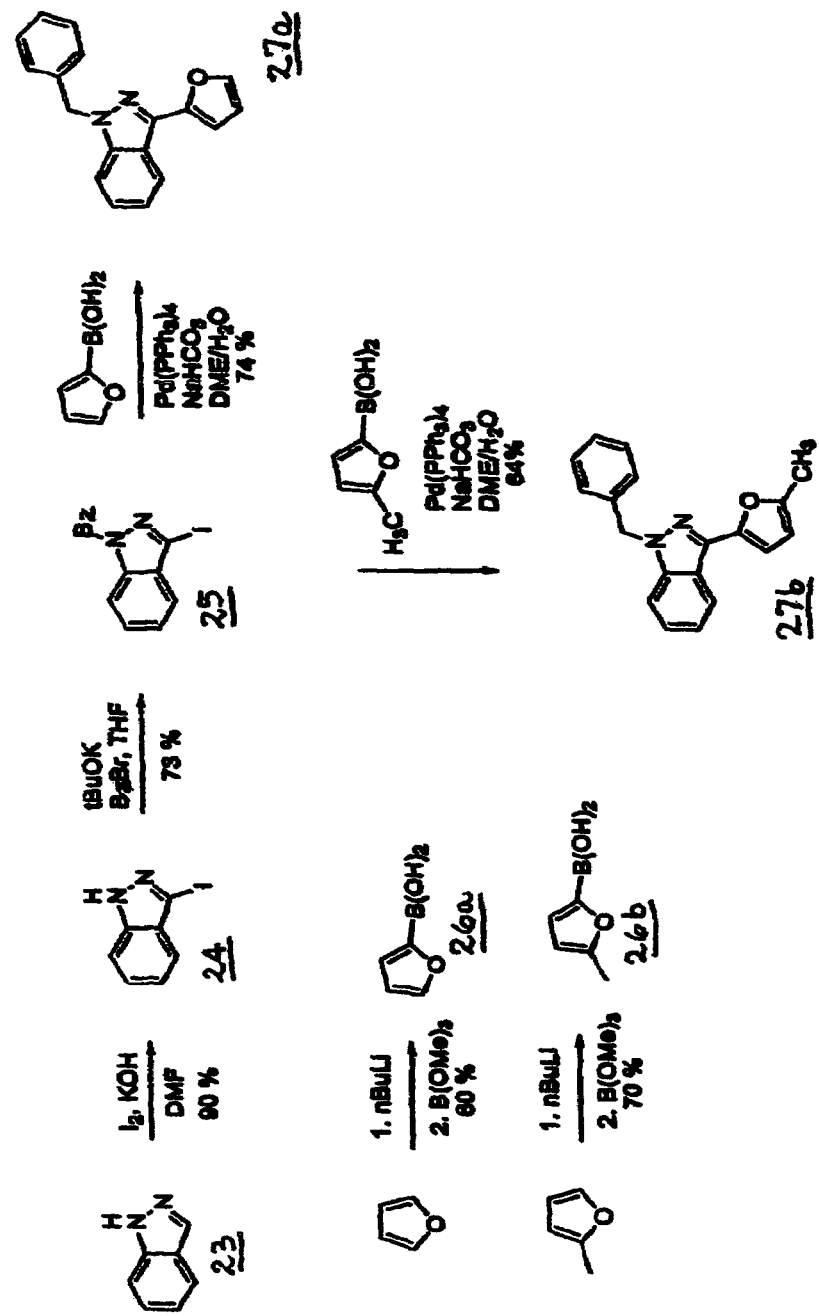

Referring to FIG. 11, there is shown a scheme for making 3-furanyl indazoles. 3-Iodo-indazole 24 is sequentially alkylated and arylated at positions 1- and 3- to produce 27a or 27b. The reagents 26a and 26b are formed from the appropriate furan.

Figure 12A:
Figure 12B:
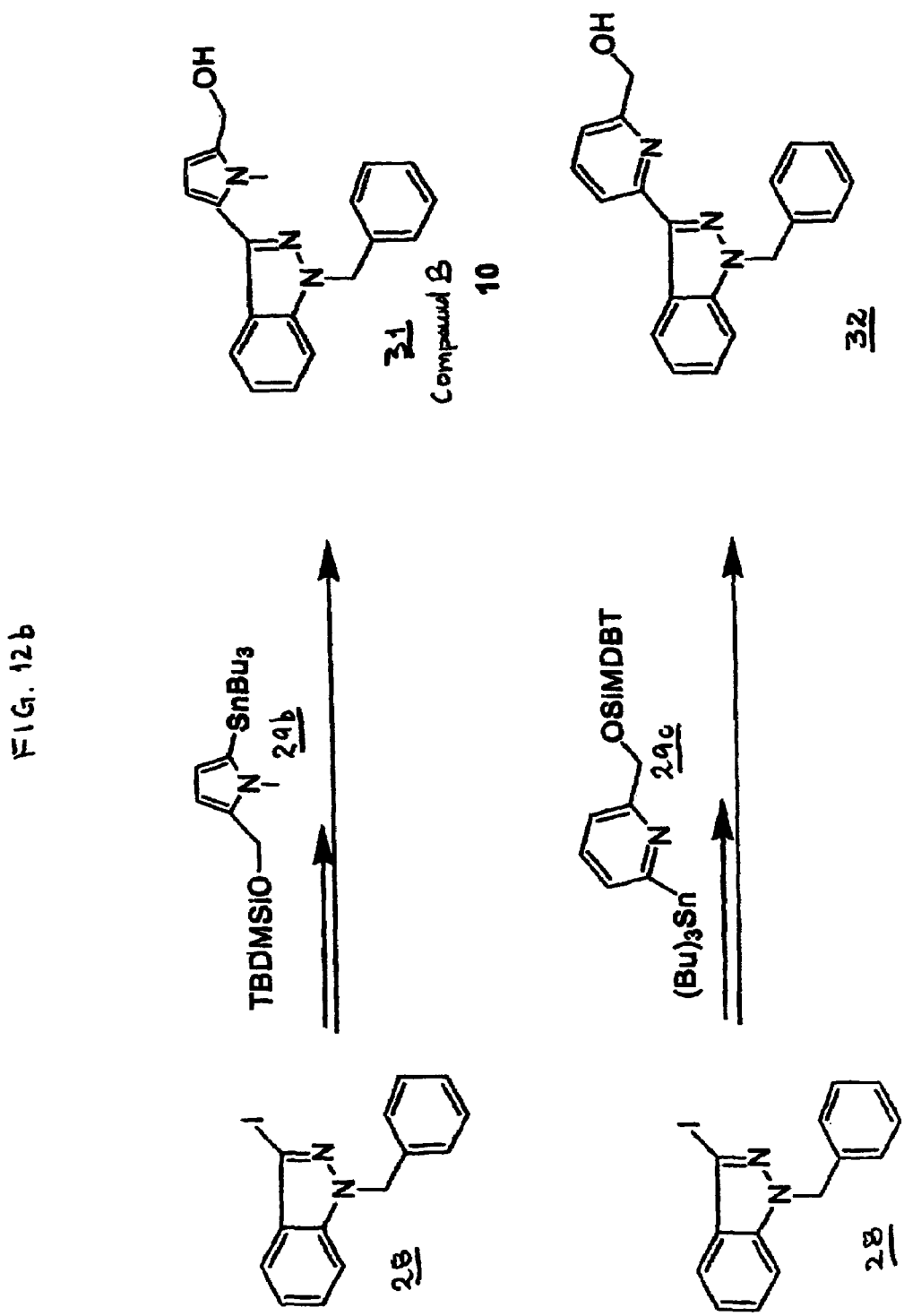

FIGS. 12a and 12b illustrate schemes for making 3-arylated 1-benzyl indazoles from a common precursor, 1-benzyl-3-iodoindazole 28, made from 3-iodo-indazole 16. The reagents 29b and 29c are made by a method analogous to that shown for making reagent 29a from an appropriate haloaryl compound. The 3-arylated compounds 30, 31 and 32 are made in one step from 28. Compound 31 is also identified as Compound B herein.

Figure 13:
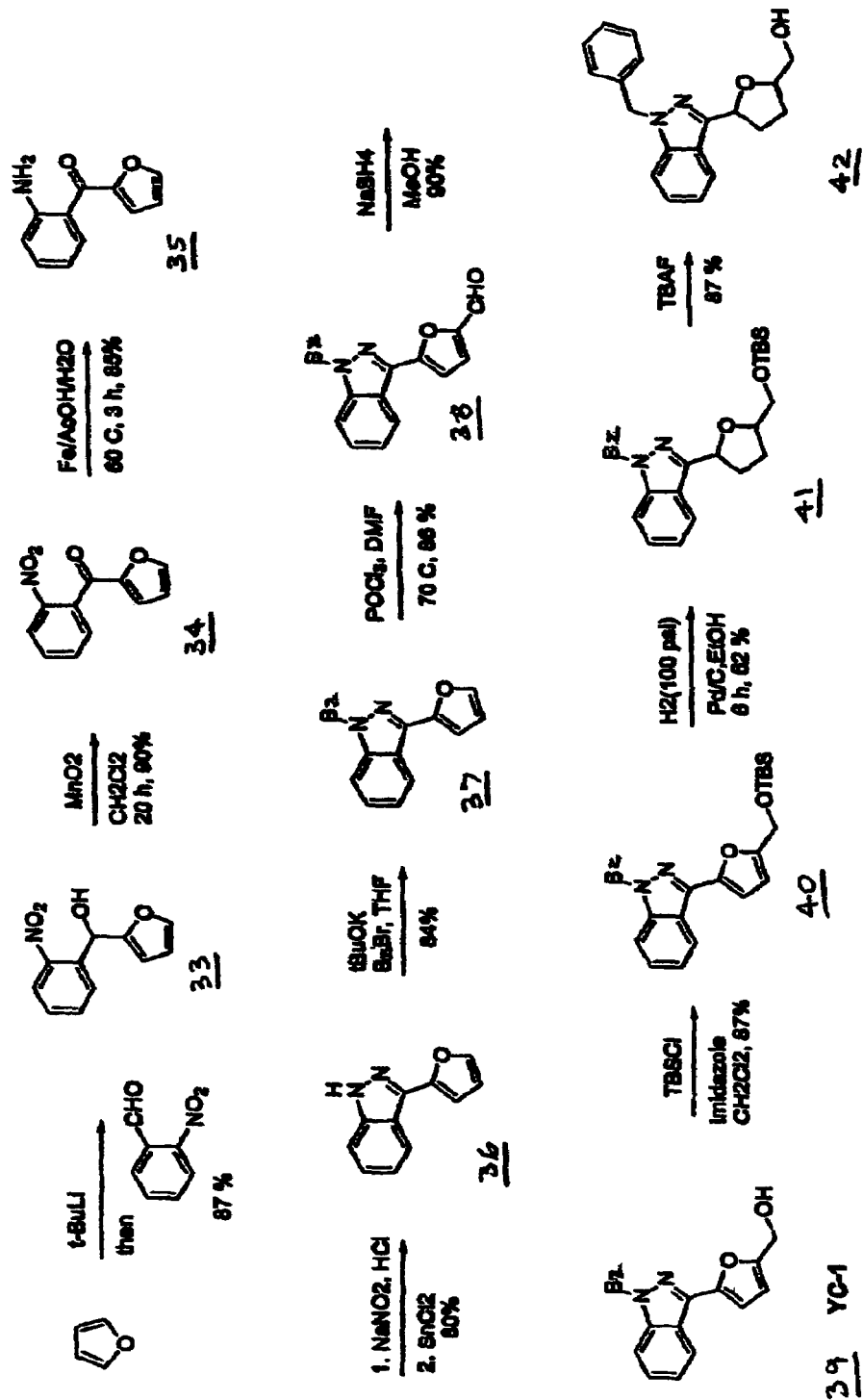

Referring to FIG. 13 there is shown another scheme for making 1,3-substituted indazoles. Condensation, mild oxidation, selective reduction of the nitro goup, nitration and cyclization result in 1-furanyl-indazole 36. Benzylation and carbonylation produce the 1-benzyl-3-furanyl indazole 39, also identified as YC-1. The furanyl ring is then reduced to produce the 3-tetrahyrofuranyl indazole 42.

Figure 14:
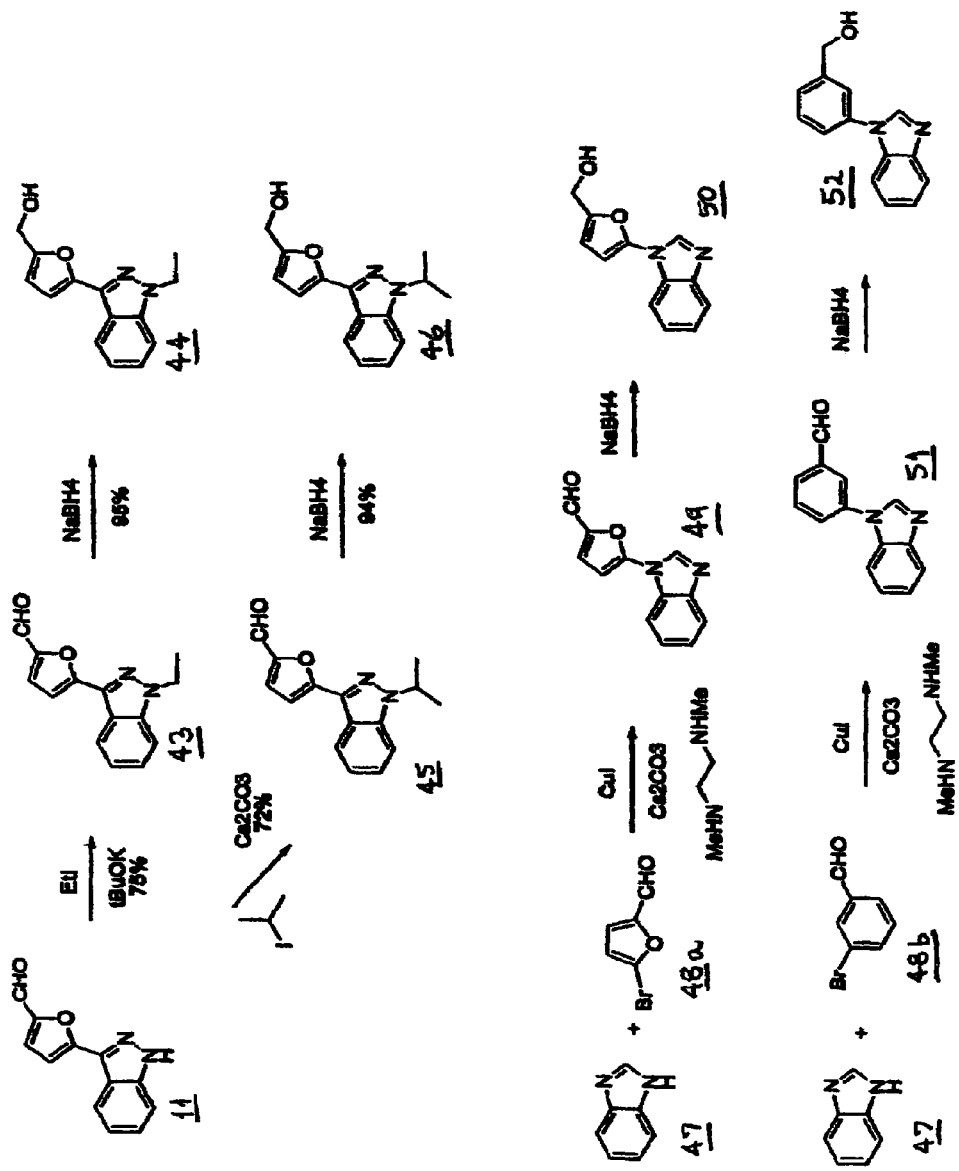

Referring to FIG. 14 there are shown a scheme to produce 1-alkyl indazoles and 1-aryl benzimidazoles. The 3-furanyl indazole 11 N-alkylated and reduced to produce the N-ethyl or N-1-propyl indazole 44 or 46. The benzimidazoles 49 and 51 are respectively formed from isoindole 47 and an appropriate haloaryl compound 48a or 48b. Reduction produces the 1-arylated benzimidazoles 50 and 52.

Figure 15:
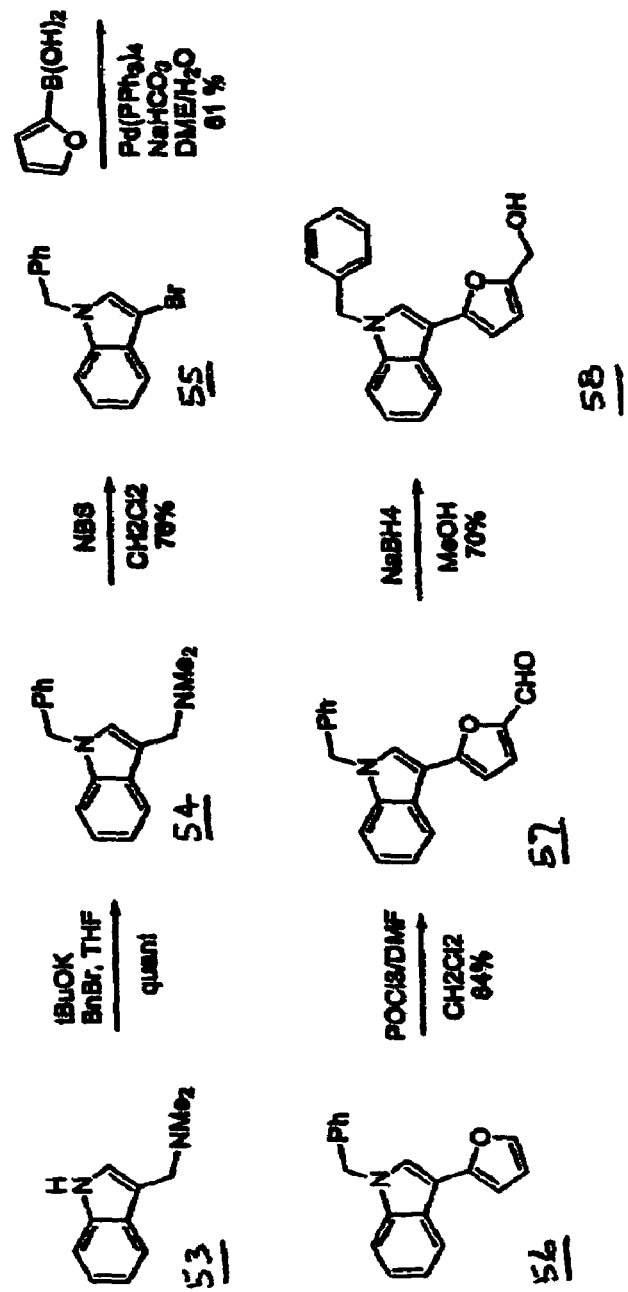

Referring to FIG. 15 there is shown a scheme for producing 1,3, substituted-indole. The 3-dimethylamino-indole 53 is N-alkylated, brominated, arylated, carbonylated and reduced to produce the indole 58.

Figure 16:
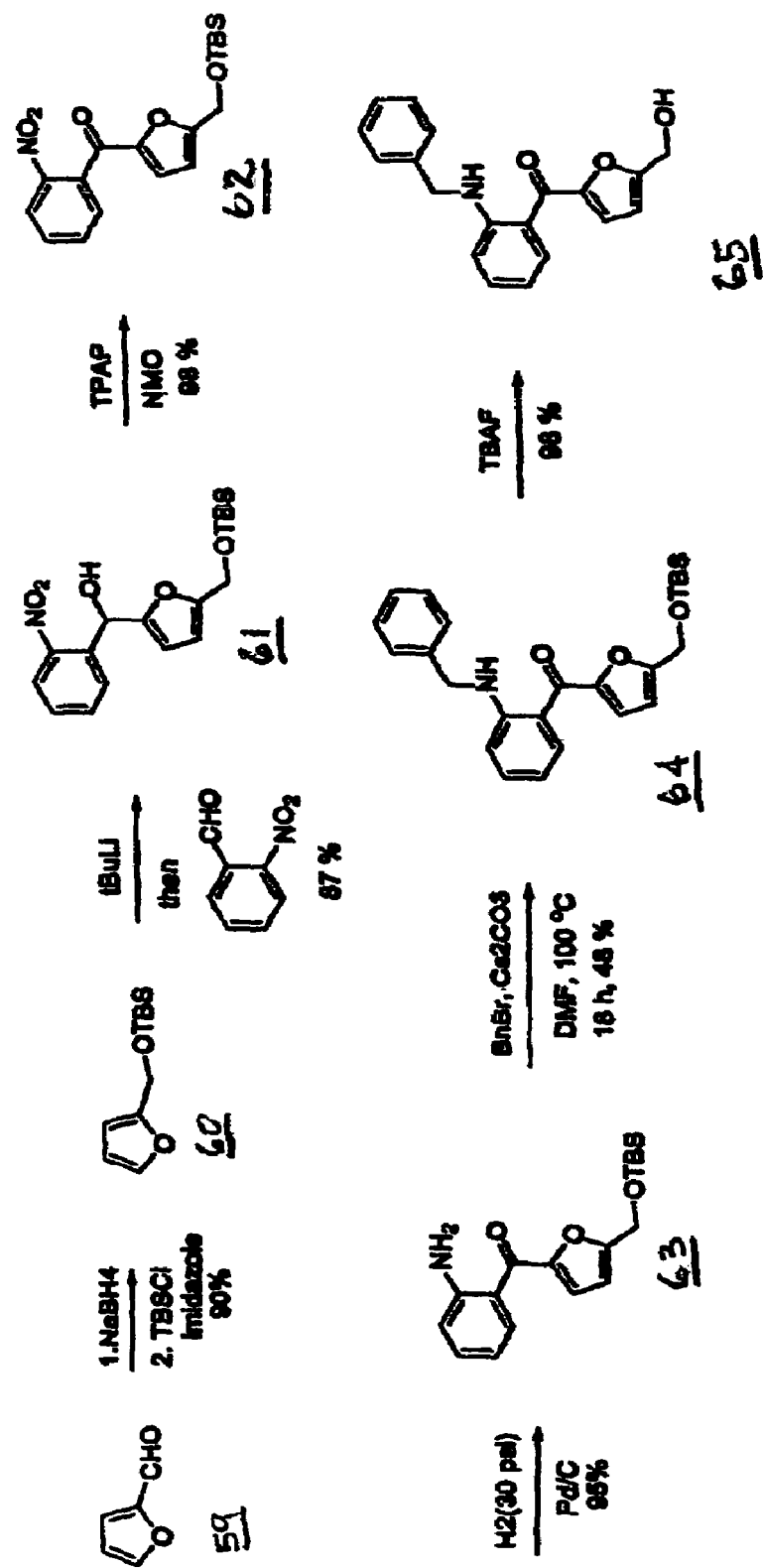

FIG. 16 shows a scheme for making some compounds of the Formula II. Reduction of the aldehyde 59, followed by activation and condensation produce the bicyclic compound 61. Oxidation, selective reduction of the nitro group, N-alkylation and deprotection results in the compound 65.

Figure 17:
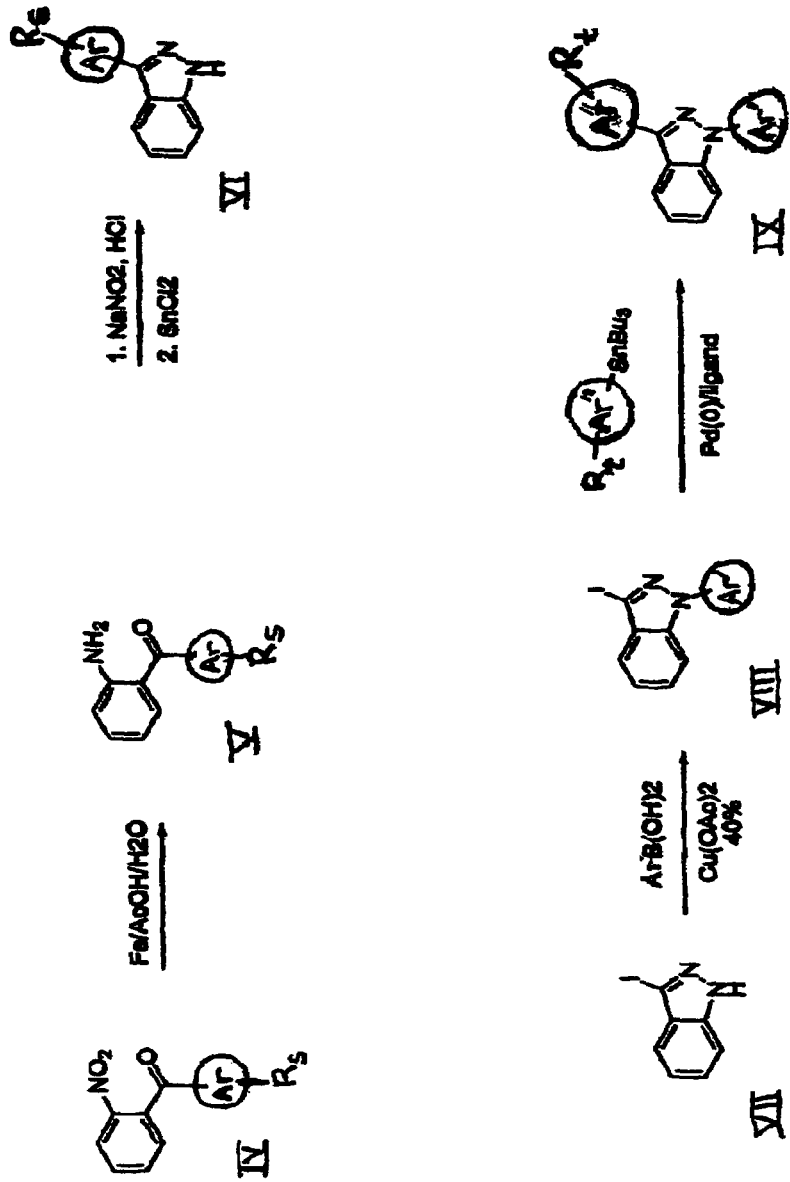

Referring to FIG. 17, there are shown two general schemes for synthesizing intermediates useful for preparation of compounds of the invention. Compound IV may be readily prepared by acylation methods known in the art. The group Ar is an aryl or heteroaryl group, optionally substituted with $R_s$ which may a group defined herein under the definition "substituted-". Reduction with iron in aqueous acetic acid produces the amine IV which is then cyclized to the 3-substituted indazole VI with sodium nitrite in acid, followed by stannous chloride. The intermediate VI is useful for preparing compounds according to the invention.

Still referring to FIG. 17, 3-iodo-indazole VII is treated with the dihydroxyborane Ar'B(OH)$_2$ where Ar' is aryl or heteroaryl, followed by cupric diacetate, yielding the 1-substituted iodo-indazole VIII. Then VIII is treated with an appropriate tributyl-tin compound $R_t$—Ar"—SnBu$_3$ in palladium catalyst. The group Ar" is aryl or heteroaryl. The substituent $R_t$ is a group defined herein under the definition "substituted-". This produces the 1,3-substituted indazole IX which is a useful intermediate for making compounds according to the invention. Ar and Ar" are independently preferably heteroaryl and Ar' is preferably aryl.

It is understood that other schemes may be devised to produce compounds within the scope of the invention. It is understood also that it is within the skill of those of ordinary skill in the art, given these reaction schemes, to select appropriate solvents, reaction temperatures, ratios, etc. to accomplish the steps indicated to produce a useful amount of the indicated product.

Unless specified to the contrary, the reactions described herein take place at atmospheric pressure, generally within a temperature range from −100° C. to 110° C. Further, except as employed in the Examples or as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The terms "solvent", "organic solvent" or "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can, of course, also be used.

When desired, the (R)— and (S)—isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. For example, a compound of Formula I or II can be dissolved in a lower alkanol and placed on a Chiralpak AD (205×20 mm) column (Chiral Technologies, Inc.) conditioned for 60 min at 70% EtOAc in hexane. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

While it is well known that pharmaceuticals must meet pharmacopoeia standards before approval and/or marketing, and that synthetic reagents and precursors should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a synthetic process of the invention.

Preferred Processes and Last Steps

A racemic mixture of isomers of a compound of Formula I or II is placed on a chromatography column and separated into (R)— and (S)— enantiomers.

A compound of Formula I or II is contacted with a pharmaceutically acceptable base to form the corresponding base addition salt.

A pharmaceutically acceptable acid addition salt of Formula I or II is contacted with an acid to form the corresponding compound of Formula I or II. A compound of Formula I or II is contacted with a pharmaceutically acceptable acid to form the corresponding acid addition salt.

A pharmaceutically acceptable acid addition salt of Formula I or II is contacted with a base to form the corresponding free base of Formula I or II.

Preferred Compound

Preferred for the compounds, pharmaceutical formulations, methods of manufacture and use of the present invention are the following combinations and permutations of substituent groups of Formula I (sub-grouped, respectively, in increasing order of preference).

In a particular embodiment, X is N, and Y is C.

In another embodiment, X is CH and Y is N.

In one embodiment, $R_1$ is furanyl; phenyl; pyridinyl; thiophenyl; benzyl; diazole; triazole; tetrahydrofuranyl; or pyrrolyl-, each of which may be optionally substituted with one, two or three (especially one) of the following groups:
lower-alkyl (especially methyl);
amino-substituted lower-alkyl (especially aminomethyl-);
hydroxy-substituted lower-alkyl- (especially hydroxymethyl-, hydroxyethyl-, 1-hydroxy-1-methyl-ethyl-; or hydroxyethoxymethyl-);
(lower-alkoxy)methyl- (especially methoxymethyl- or ethoxymethyl-); or
(lower-alkyl)sulfanyl- (especially methylsulfanyl-).

In another embodiment, $R_1$ is optionally substituted benzyl or optionally substituted phenyl.

More particularly, $R_1$ is hydroxymethylpyridinyl-; hydroxymethylphenyl-; hydroxymethylfuranyl-; aminomethylfuranyl-; methoxymethylfuranyl-; hydroxy-ethoxymethyl-furanyl-; (1-hydroxy-ethyl)-furanyl-; (1-hydroxy-1-methyl-ethyl)-furanyl-; hydroxymethyltetrahydrofuranyl-; hydroxymethylthiophenyl-; hydroxymethylpyrrolyl-; or hydroxymethyl-N-methyl-pyrrolyl.

In another embodiment, $R_1$ is optionally substituted benzyl or optionally substituted phenyl.

In another embodiment, $R_1$ is optionally substituted alkyl, preferably lower alkyl.

In one embodiment, $R_2$ and $R_3$ are hydrogen.

In another embodiment, $R_2$ and $R_3$, together with the carbons to which they are attached, form a fused benzo- or pyridino ring, which may be optionally substituted with one or more of the following groups: halo (especially fluoro or chloro); optionally substituted lower-alkyl (especially methyl or trifluoromethyl); lower-alkoxy (especially methoxy); hydroxy; cyano; nitro; or optionally substituted amino (especially amino, methylamino, or acetylamino).

In a particular embodiment, $R_4$ is optionally substituted phenyl; optionally substituted benzyl; optionally substituted cyclohexylmethyl-; optionally substituted phenethyl-; optionally substituted pyridinylmethyl-; optionally substituted furanyl-; or optionally substituted pyrrolyl- optionally substituted thienyl, optionally substituted triazole, optionally substituted thienylmethyl, optionally substituted diazole; optionally substituted alkyl. More particularly, the aforementioned ring systems may be substituted with one or more of the following groups: halo (especially fluoro or chloro); optionally substituted lower-alkyl (especially methyl or trifluoromethyl); lower-alkoxy (especially methoxy); hydroxy; cyano; nitro; or optionally substituted amino.

In another embodiment, $R_4$ is optionally substituted alkyl, preferably lower alkyl.

A preferred class of compounds includes those in which $R_1$ is optionally substituted heterocyclyl, provided that when Y=N and X=CH, $R_1$ is absent; and $R_4$ is aryl of 5 to 14 carbon atoms or alkyl of 1 to 10 carbon atoms, except that when Y=N and X=CH, $R_1$ may be optionally substituted heterocyclyl. In this class $R_2$ and $R_3$ are independently H, optionally substituted alkyl, or $R_2$ and $R_3$ together with the carbon atoms to which they are attached form an optionally substituted aryl or optionally substituted heteroaryl ring. Subclasses of this preferred class include those in which X=N, Y=C and $R_4$ is alkyl of 1 to 10 carbon atoms; X=N, Y=C and $R_4$ is aryl of 5 to 14 carbon atoms; X=CH and Y=N; and $R_2$ and $R_3$ are joined to form a 6-membered aryl ring.

More preferred (individually and collectively) as novel compounds of the present invention, including their formulations, methods of manufacture and use, are the following:
[5-(1-Methyl-1H-indazol-3-yl)-furan-2-yl]-methanol (Compound A);
[5-(1H-Indazol-3-yl)-furan-2-yl]-methanol;
[5-(1-Benzyl-1H-pyrazol-3-yl)-furan-2-yl]-methanol;
1-Benzyl-1H-indazole;
1-Benzyl-3-furan-2-yl-1H-indazole;
1-Benzyl-3-(5-methyl-furan-2-yl)-1H-indazole;
1-Benzyl-3-(5-methoxymethyl-furan-2-yl)-1H-indazole;
2-[5-(1-Benzyl-1H-indazol-3-yl)-furan-2-yl]-propan-2-ol;
2-[5-(1-Benzyl-1H-indazol-3-yl)-furan-2-ylmethoxy]-ethanol;
1-[5-(1-Benzyl-1H-indazol-3-yl)-furan-2-yl]-ethanol;
[5-(1-Benzyl-1H-indazol-3-yl)-tetrahydro-furan-2-yl]-methanol;
C-[5-(1-Benzyl-1H-indazol-3-yl)-furan-2-yl]-methylamine;
[5-(1-Benzyl-1H-indazol-3-yl)-furan-3-yl]-methanol;
[5-(1-Benzyl-1H-indazol-3-yl)-thiophen-2-yl]-methanol;
[5-(1-Benzyl-1H-indazol-3-yl)-1-methyl-1H-pyrrol-2-yl]-methanol;
[5-(1-Benzyl-1H-indazol-3-yl)-1H-pyrrol-2-yl]-methanol;
[4-(1-Benzyl-1H-indazol-3-yl)-phenyl]-methanol;
[6-(1-Benzyl-1H-indazol-3-yl)-pyridin-3-yl]-methanol;
[5-(1-Benzyl-1H-indazol-3-yl)-pyridin-2-yl]-methanol;
[3-(1-Benzyl-1H-indazol-3-yl)-phenyl]-methanol;
[4-(1-Benzyl-1H-indazol-3-yl)-pyridin-2-yl]-methanol;
[6-(1-Benzyl-1H-indazol-3-yl)-pyridin-2-yl]-methanol;
[6-(1-Benzyl-1H-indazol-3-yl)-pyridin-2-yl]-methanol;

4-[3-(5-Hydroxymethyl-furan-2-yl)-indazol-1-ylmethyl]-phenol;
{5-[1-(4-Amino-benzyl)-1H-indazol-3-yl]-furan-2-yl}-methanol;
{5-[1-(4-Fluoro-benzyl)-1H-indazol-3-yl]-furan-2-yl}-methanol;
{5-[1-(4-Nitro-benzyl)-1H-indazol-3-yl]-furan-2-yl}-methanol;
{5-[1-(4-Trifluoromethyl-benzyl)-1H-indazol-3-yl]-furan-2-yl}-methanol;
{5-[1-(4-Methoxy-benzyl)-1H-indazol-3-yl]-furan-2-yl}-methanol;
{5-[1-(4-Chloro-benzyl)-1H-indazol-3-yl]-furan-2-yl}-methanol;
{5-[1-(4-Cyano-benzyl)-1H-indazol-3-yl]-furan-2-yl}-methanol;
{5-[1-(3-Amino-benzyl)-1H-indazol-3-yl]-furan-2-yl}-methanol;
{5-[1-(3-Fluoro-benzyl)-1H-indazol-3-yl]-furan-2-yl}-methanol;
{5-[1-(3-Nitro-benzyl)-1H-indazol-3-yl]-furan-2-yl}-methanol;
{5-[1-(3-Trifluoromethyl-benzyl)-1H-indazol-3-yl]-furan-2-yl}-methanol;
{5-[1-(3-Methoxy-benzyl)-1H-indazol-3-yl]-furan-2-yl}-methanol;
{5-[1-(3-Chloro-benzyl)-1H-indazol-3-yl]-furan-2-yl}-methanol;
{5-[1-(3-Cyano-benzyl)-1H-indazol-3-yl]-furan-2-yl}-methanol;
{5-[1-(3-methyl-benzyl)-1H-indazol-3-yl]-furan-2-yl}-methanol;
{5-[1-(2-Amino-benzyl)-1H-indazol-3-yl]-furan-2-yl}-methanol;
{5-[1-(2-Fluoro-benzyl)-1H-indazol-3-yl]-furan-2-yl}-methanol;
{5-[1-(2-Nitro-benzyl)-1H-indazol-3-yl]-furan-2-yl}-methanol;
{5-[1-(2-Trifluoromethyl-benzyl)-1H-indazol-3-yl]-furan-2-yl}-methanol;
{5-[1-(2-Methoxy-benzyl)-1H-indazol-3-yl]-furan-2-yl}-methanol;
{5-[1-(2-Chloro-benzyl)-1H-indazol-3-yl]-furan-2-yl}-methanol;
{5-[1-(2-Cyano-benzyl)-1H-indazol-3-yl]-furan-2-yl}-methanol;
{5-[1-(2-Methyl-benzyl)-1H-indazol-3-yl]-furan-2-yl}-methanol;
3-[3-(5-Hydroxymethyl-furan-2-yl)-indazol-1-ylmethyl]-phenol;
2-[3-(5-Hydroxymethyl-furan-2-yl)-indazol-1-ylmethyl]-phenol;
[5-(1-Pyridin-2-ylmethyl-1H-indazol-3-yl)-furan-2-yl]-methanol;
[5-(1-Pyridin-3-ylmethyl-1H-indazol-3-yl)-furan-2-yl]-methanol;
[5-(1-Pyridin-4-ylmethyl-1H-indazol-3-yl)-furan-2-yl]-methanol;
[5-(1-Cyclohexylmethyl-1H-indazol-3-yl)-furan-2-yl]-methanol;
[5-(1-Furan-3-ylmethyl-1H-indazol-3-yl)-furan-2-yl]-methanol;
[5-(1-Thiophen-3-ylmethyl-1H-indazol-3-yl)-furan-2-yl]-methanol;
{5-[1-(1-Methyl-1H-pyrrol-3-ylmethyl)-1H-indazol-3-yl]-furan-2-yl}-methanol;
{5-[1-(1H-Pyrrol-3-ylmethyl)-1H-indazol-3-yl]-furan-2-yl}-methanol;
[5-(1-Furan-2-ylmethyl-1H-indazol-3-yl)-furan-2-yl]-methanol;
[5-(1-Thiophen-2-ylmethyl-1H-indazol-3-yl)-furan-2-yl]-methanol;
{5-[1-(1-Methyl-1H-pyrrol-2-ylmethyl)-1H-indazol-3-yl]-furan-2-yl}-methanol;
{5-[1-(1H-Pyrrol-2-ylmethyl)-1H-indazol-3-yl]-furan-2-yl}-methanol;
[5-(1-Phenethyl-1H-indazol-3-yl)-furan-2-yl]-methanol;
[5-(1-Benzyl-1H-pyrazolo[3,4-b]pyridin-3-yl)-furan-2-yl]-methanol;
[5-(1-Phenyl-1H-indazol-3-yl)-furan-2-yl]-methanol;
[5-(1-Benzyl-1H-pyrazolo[4,3-b]pyridin-3-yl)-furan-2-yl]-methanol;
[5-(1-Benzyl-5-methyl-1H-indazol-3-yl)-furan-2-yl]-methanol;
[5-(1-Benzyl-5-trifluoromethyl-1H-indazol-3-yl)-furan-2-yl]-methanol;
[5-(1-Benzyl-5-hydroxy-1H-indazol-3-yl)-furan-2-yl]-methanol;
[5-(1-Benzyl-5-amino-1H-indazol-3-yl)-furan-2-yl]-methanol;
[5-(1-Benzyl-5-fluoro-1H-indazol-3-yl)-furan-2-yl]-methanol;
[5-(1-Benzyl-5-methoxy-1H-indazol-3-yl)-furan-2-yl]-methanol;
[5-(1-Benzyl-5-nitro-1H-indazol-3-yl)-furan-2-yl]-methanol;
[5-(1-Benzyl-5-cyano-1H-indazol-3-yl)-furan-2-yl]-methanol;
[5-(1-Benzyl-5-chloro-1H-indazol-3-yl)-furan-2-yl]-methanol;
[5-(1-Benzyl-6-methyl-1H-indazol-3-yl)-furan-2-yl]-methanol;
[5-(1-Benzyl-6-trifluoromethyl-1H-indazol-3-yl)-furan-2-yl]-methanol;
[5-(1-Benzyl-6-hydroxy-1H-indazol-3-yl)-furan-2-yl]-methanol;
[5-(1-Benzyl-6-amino-1H-indazol-3-yl)-furan-2-yl]-methanol;
[5-(1-Benzyl-6-fluoro-1H-indazol-3-yl)-furan-2-yl]-methanol;
[5-(1-Benzyl-6-methoxy-1H-indazol-3-yl)-furan-2-yl]-methanol;
[5-(1-Benzyl-6-nitro-1H-indazol-3-yl)-furan-2-yl]-methanol;
[5-(1-Benzyl-6-cyano-1H-indazol-3-yl)-furan-2-yl]-methanol; or
[5-(1-Benzyl-6-chloro-1H-indazol-3-yl)-furan-2-yl]-methanol. {5-[(3-Benzyl)-1H -indazol-3-yl-]-furan-2-yl}-methanol
(2'-Hydroxymethyl)-(2-benzyl)-1H-indazo[6,7:5'4']furan
{5-[V-benzimidazol-1-yl]-furan-2-yl}-methanol
{5-[(7-Phenyl)-1H-indazol-3-yl]-furan-2-yl}-methanol
{5-[1-Methyl-1H-benzimidazol-4-yl]-furan-2-yl}-methanol
{5-[1-Ethyl-1H-indazol-3-yl]-furan-2-yl}-methanol
{5-[1-(Prop-2-yl)-1H-indazol-3-yl]-furan-2-yl}-methanol
{5-[1-(2-Methyl-prop-2-yl)-1H-indazol-3-yl]-furan-2-yl}-methanol
{5-[(1-(Furan-2'-yl)-methyl)-1H-indazol-3-yl]-furan-2-yl}-methanol
{5-[(1-(Thien-2'-yl)-methyl)-1H-indazol-3-yl]-furan-2-yl}-methanol
{5-[(1-(N-Methyl-pyrrol-2'yl)-methyl)-1H-indazol-3-yl]-furan-2-yl}-methanol {5-[(1-(Furan-3'-yl)-methyl)-1H-indazol-3-yl]-furan-2-yl]-furan-2-yl}-methanol
{5-[(1-(Thien-3'-yl)-methyl)-1H-indazol-3-yl]-furan-2-yl}-methanol
{5-[(1-(N-Methyl-pyrrol-3'yl)-methyl)-1H-indazol-3-yl]-furan-2-yl}-methanol
{5-[(1-(Oxa-3',4'-diazol-2'-yl)-methyl)-1H-indazol-3-yl]-furan-2-yl}-methanol
{5-[(1-(Pyrrol-1'-yl)-methyl)-1H-indazol-3-yl]-furan-2-yl}-methanol
{5-[(1-(Thia-3',4'-diazol-2'-yl)-methyl)-1H-indazol-3-yl]-furan-2-yl}-methanol
{5-[(1-(4'-Methyl-1',2',4'-triazol-5'-yl)-methyl)-1H-indazol-3-yl]-furan-2-yl}-methanol
{5-[(1-(1',2',4'-Triazol-1'-yl)-methyl)-1H-indazol-3-yl]-furan-2-yl}-methanol
{5-[(1-(1',2',4'-Triazol-4'-yl)-methyl)-1H-indazol-3-yl]-furan-2-yl}-methanol
{5-[(1-(1',3'-Oxazol-2'-yl)-methyl)-1H-indazol-3-yl]-furan-2-yl}-methanol
{5-[(1-(1',3'-Thiazol-2'-yl)-methyl)-1H-indazol-3-yl]-furan-2-yl}-methanol
{5-[(1-(1'-Methyl-1',3'-diazol-2'-yl)-1H methyl)-1H-indazol-3-yl]-furan-2-yl}-methanol
{5-[(1-(1',3'-Oxazol-5'-yl)-methyl)-1H-indazol-3-yl]-furan-2-yl}-methanol
{5-[(1-(1',3'-Thiazol-5'-yl)-methyl)-1H-indazol-3-yl]-furan-2-yl}-methanol
{5-[(1-(1'-Methyl-1'3'-diazol-5'-yl)-methyl)-1H-indazol-3-yl]-furan-2-yl}-methanol
{5-[(1-(1',3'-Oxazol-4'-yl)-methyl)-1H-indazol-3-yl]-furan-2-yl}-methanol
{5-[(1-(1',3'-Thiazol-4'-yl)-methyl)-1H-indazol-3-yl]-furan-2-yl}-methanol
{5-[(1-(1'-Methyl-1',2'-diazol-5'-yl)-methyl)-1H1H-indazol-3-yl]-furan-2-yl}-methanol
{5-[(1-(1'-Methyl-1',3'-diazol-4'-yl)-methyl)-1H-indazol-3-yl]-furan-2-yl}-methanol
{5-[(1-(1',3'-Diazol-1'-yl)-methyl)-1H-indazol-3-yl]-furan-2-yl}-methanol
{5-[(1-(1'-Methyl-1',2'-diazol-4'-yl)-methyl)-1H-indazol-3-yl]-furan-2-yl}-methanol
{5-[(1-(1'-Methyl-1',2'-diazol-3'-yl)-methyl)-1H-indazol-3-yl]-furan-2-yl}-methanol
{5-[(1-(1',2'-Diazol-1'-yl)-methyl)-1H-indazol-3-yl]-furan-2-yl}-methanol
{5-[(1-(Furan-2'-yl)-methyl)-1H-indazol-3-yl]-furan-2-yl}-methanol
{5-[(1-(Thien-2'-yl)-methyl)-1H-indazol-3-yl]-furan-2-yl}-methanol
{5-[(1-(N-methyl-pyrrol-2'-yl)-1H-indazol-3-yl]-furan-2-yl}-methanol
{5-[(1-(Pyrrol-1'-yl)-methyl)-1H-indazol-3-yl]-furan-2-yl}-methanol
{5-[(1-(Furan-3'-yl)-1H-indazol-3-yl]-furan-2-yl}-methanol
{5-[(1-(Thien-3'-yl)-methyl)-1H-indazol-3-yl]-furan-2-yl}-methanol
{5-[(1-(N-Methyl-pyrrol-3'-yl)-1H-indazol-3-yl]-furan-2-yl}-methanol
{5-[(1-(4'-Methyl-1',2',4'-triazol-5'-yl)-1H-indazol-3-yl]-furan-2-yl}-methanol
{5-[(1-(1',2',4'-Triazol-4'-yl)-1H-indazol-3-yl]-furan-2-yl}-methanol
{5-[(1-(Thia-3'-4'diazol-2'-yl)-1H-indazol-3-yl]-furan-2-yl}-methanol
{5-[(1-(1',3'-Oxazol-2'-yl)-1H-indazol-3-yl]-furan-2-yl}-methanol
{5-[(1-(1',3'-Thiazol-2'-yl)-1H-indazol-3-yl]-furan-2-yl}-methanol
{5-[(1-(1'-Methyl-1',3'-diazol-2'-yl)-1H-indazol-3-yl]-furan-2-yl}-methanol
{5-[(1-(1',3'-Oxazol-4'-yl)-1H-indazol-3-yl]-furan-2-yl}-methanol
{5-[(1-(1',3'-Thiazol-4'-yl)-1H-indazol-3-yl]-furan-2-yl}-methanol
{5-[(1-(1'-Methyl-1,3'-diazol)-4'-yl)-1H-indazol-3-yl]-furan-2-yl}-methanol
{5-[(1-(1',3-Diazol-1'-yl)-1H-indazol-3-yl]-furan-2-yl}-methanol
{5-[(1-(1',3'-Oxazol-5'-yl)-1H-indazol-3-yl]-furan-2-yl}-methanol
{5-[(1-(1',3'-Thiazol-5'-yl)-1H-indazol-3-yl]-furan-2-yl}-methanol
{5-[(1-(1'-Methyl-1',3'-diazol-5'-yl)-1H-indazol-3-yl]-furan-2-yl}-methanol
{5-[(1-(1'-Methyl-1',2'-diazol-5'-yl)-1H-indazol-3-yl]-furan-2-yl}-methanol
{5-[(1-(1',2'-Diazol-1'-yl)-1H-indazol-3-yl]-furan-2-yl}-methanol
{5-[(1-(1'-Methyl-1',2'-diazol-3'-yl)-1H-indazol-3-yl]-furan-2-yl}-methanol
{5-[(1-(1'-Methyl-1',2'-diazol-4'-yl)-1H-indazol-3-yl]-furan-2-yl}-methanol
{5-[1-Benzyl-1H-indazol-3-yl]-furan-3-yl}-methanol
{5-[1-Benzyl-1H-indazol-3-yl]-thien-3-yl}-methanol
{N-Methyl-5-[benzyl-1H-indazol-3-yl]-pyrrol-3-yl}-methanol
{4-[1-Benzyl-1H-indazol-3-yl]-furan-2-yl}-methanol
{4-[1-Benzyl-1H-indazol-3-yl]-thien-2-yl}-methanol
{N-Methyl-4-[1-benzyl-1H-indazol-3-yl]-pyrrol-2-yl}-methanol
{4-Methyl-5-[1-benzyl-1H-indazol-3-yl]-1,2,4-triazol-3-yl}-methanol
{5-[1-Benzyl-1H-indazol-3-yl]-thien-2-yl}-methanol
{N-Methyl-5-[1-benzyl-1H-indazol-3-yl]-pyrrol-2-yl}-methanol (Compound B)
{1-[1-Benzyl-1H-indazol-3-yl]-1,2,4-triazol-3-yl}-methanol
{1-[1-Benzyl-1H-indazol-3-yl]-pyrrol-3-yl}-methanol
{5-[1-Benzyl-1H-indazol-3-yl]-oxa-3-4-diazol-2-yl}-methanol
{5-[1-Benzyl-1H-indazol-3-yl]-thia-3,4-diazol-2-yl}-methanol
{1-[1-Benzyl-1H-indazol-3-yl]-1,2-diazol-4-yl}-methanol
{1-[1-Benzyl-1H-indazol-3-yl]-1,2-diazol-3-yl}-methanol
{1-Methyl-3-[1-benzyl-1H-indazol-3-yl]-1,2-diazol-5-yl}-methanol
{1-Methyl-5-[1-benzyl-1H-indazol-3-yl]-1,2-diazol-3-yl}-methanol
{1-[1-Benzyl-1H-indazol-3-yl]-1,3-diazol-4-yl}-methanol
{2-[1-Benzyl-1H-indazol-3-yl]-1,3-oxazol-5-yl}-methanol
{2-[1-Benzyl-1H-indazol-3-yl]-1,3-thiazol-5-yl}-methanol
{1-Methyl-2-[1-benzyl-1H-indazol-3-yl]-1,3-diazol-5-yl}-methanol
{5-[1-Benzyl-1H-indazol-3-yl]-1,3-oxazol-5-yl}-methanol
{2-[1-Benzyl-1H-indazol-3-yl]-1,3-oxazol-4-yl}-methanol
{2-[1-Benzyl-1H-indazol-3-yl]-1,3-thiazol-4-yl}-methanol
{1-Methyl-2-[1-benzyl-1H-indazol-3-yl]-1,3-diazol-4-yl}-methanol
{1-Methyl-5-[1-benzyl-1H-indazol-3-yl]-1,3-diazol-2-yl}-methanol
{4-[1-Benzyl-1H-indazol-3-yl]-1,3-oxazol-2-yl}-methanol
{4-[1-Benzyl-1H-indazol-3-yl]-1,3-thiazol-2-yl}-methanol {1-Methyl-4-[1-benzyl-1H-indazol-3-yl]-1,3-diazol-2-yl}-methanol
{5-[1-Benzyl-1H-indazol-3-yl]-1,3-thiazol-2-yl}-methanol
{2-[1-Phenyl-1H-indazol-3-yl]-1,3-oxazol-5-yl}-methanol
{2-[1-Phenyl-1H-indazol-3-yl]-1,3-thiazol-5-yl}-methanol
{1-Methyl-2-[1-phenyl-1H-indazol-3-yl]-1,3-diazol-5-yl}-methanol
{2-[1-Phenyl-1H-indazol-3-yl]-1,3-oxazol-4-yl}-methanol
{2-[1-Phenyl-1H-indazol-3-yl]-1,3-thiazol-4-yl}-methanol
{1-Methyl-2-[1-phenyl-1H-indazol-3-yl]-1,3-diazol-4-yl}-methanol
{1-[1-Phenyl-1H-indazol-3-yl]-1,3-diazol-4-yl}-methanol
{4-[1-Phenyl-1H-indazol-3-yl]-1,3-oxazol-2-yl}-methanol
{4-[1-Phenyl-1H-indazol-3-yl]-1,3-thiazol-2-yl}-methanol
{1-Methyl-4-[1-phenyl-1H-indazol-3-yl]-1,3-diazol-2-yl}-methanol
{5-[1-Phenyl-1H-indazol-3-yl]-1,3-oxazol-2-yl}-methanol
{5-[1-Phenyl-1H-indazol-3-yl]-1,3-thiazol-2-yl}-methanol
{1-Methyl-5-[1-phenyl-1H-indazol-3-yl]-1,3-diazol-2-yl}-methanol
{5-[1-Phenyl-1H-indazol-3-yl]-furan-3-yl}-methanol
{5-[1-Phenyl-1H-indazol-3-yl]-thien-3-yl}-methanol
{N-Methyl-5-[1-phenyl-1H-indazol-3-yl]-pyrrol-3-yl}-methanol
{4-[1-Phenyl-1H-indazol-3-yl]-furan-2-yl}-methanol
{4-[1-Phenyl-1H-indazol-3-yl]-thien-2-yl}-methanol
{N-Methyl-4-[1-phenyl-1H-indazol-3-yl]-pyrrol-2-yl}-methanol
{5-[1-Phenyl-1H-indazol-3-yl]-furan-2-yl}-methanol
{5-[1-Phenyl-1H-indazol-3-yl]-thien-2-yl}-methanol
{N-Methyl-5-[1-phenyl-1H-indazol-3-yl]-pyrrol-2-yl}-methanol (Compound E)
{4-Methyl-5-[1-phenyl-1H-indazol-3-yl]-1,2,4-triazol-3-yl}-methanol
{1-[1-Phenyl-1H-indazol-3-yl]-1,2,4-triazol-3-yl}-methanol
{N-[1-Phenyl-1H-indazol-3-yl]-pyrrol-3-yl}-methanol
{5-[1-Phenyl-1H-indazol-3-yl]-oxadiazol-2-yl}-methanol
{5-[1-Phenyl-1H-indazol-3-yl]-thiadiazol-2-yl}-methanol
{2-Methyl-5-[1-phenyl-1H-indazol-3-yl]-1,2-diazol-3-yl}-methanol
{1-Methyl-3-[1-phenyl-1H-indazol-3-yl]-1,2-diazol-5-yl}-methanol
{1-[1-Phenyl-1H-indazol-3-yl]-1,2-diazol-4-yl}-methanol
{1-[1-Phenyl-1H-indazol-3-yl]-1,2-diazol-3-yl}-methanol
{5-[4-Phenyl-1H-benzimidazol-1-yl]-furan-2-yl}-methanol
{N-Methyl-5-[1H-benzimidazol-1-yl]-pyrrol-2-yl}-methanol
{1-Methyl-2-[1H-benzimidazol-1-yl]-1,3-diazol-5-yl}-methanol
{3-[1H-Benzimidazol-1-yl]-benzyl alcohol
{N-Methyl-5-[1H-benzimidazol-1-yl-methyl]-pyrrol-2-yl}}-methanol
[5-(1-Thiophen-2-yl-methyl-1H-indazol-3-yl)-furan-2-yl]-methanol (Compound C)
(3-(1H-Benzo[d]imidazol-1-yl)phenyl)-methanol
2-(3-(5-(Hydroxymethyl)furan-2-yl)-1H-indazol-1-yl)-acetic acid
2-(3-(5-(Hydroxymethyl)-furan-2-yl)-1H-indazol-1-yl)-ethanol
2-((5-(1-Methyl-1H-indazol-3-yl)-furan-2-yl)methoxy)-ethanol
(1-Methyl-5-(1-methyl-1H-indazol-3-yl)-1H-pyrrol-2-yl)-methanol (Compound D)
{N-Methyl-5-[1-thiophen-2-yl-methyl-1H-indazol-3-yl]-pyrrol-2-yl}-methanol Preferred for the compounds, pharmaceutical formulations, methods of manufacture and use of the present invention are the following compounds of Formula II:
[5-(4-Benzyl-naphthalen-1-yl)-furan-2-yl]-methanol;
(2-Benzylamino-phenyl)-(5-hydroxymethyl-furan-2-yl)-methanone; or
1-[2-(5-Hydroxymethyl-furan-2-ylamino)-phenyl]-2-phenyl-ethanone.

Also preferred for the compounds, pharmaceutical formulations, methods of manufacture and use of the present invention are the following analogs of the compounds of Formula I or II:
[5-(7-Phenyl-pyrazolo[1,5-a]pyridin-2-yl)-furan-2-yl]-methanol or
2-Benzyl-2H-8-oxa-1,2-diaza-as-indacen-7-ol.

Utility, Testing and Administration

Utility

The present invention is based on the surprising discovery that compounds of Formula I or II exhibit an antitumor effect in vivo either by inhibiting HIF activity or by arresting the cell cycle essential for tumor growth and metastasis.

Accordingly, one aspect of the present invention provides a method of inhibiting HIF-1α or HIF-2α expression in tumor cells or tissues, and to induce cell cycle arrest leading to apoptosis, comprising contacting the tumor cells or tissues with a composition comprising a compound of Formula I or II at an effective amount for inducing cell cycle arrest.

Another aspect of the present invention provides a method of inhibiting HIF-regulated gene expression in tumor cells or tissues, comprising contacting the tumor cells or tissues with a composition comprising a compound of Formula I or II at an effective amount for inhibiting HIF- regulated gene expression.

A further aspect of the present invention provides a method of inhibiting tumor growth in animal tissues, comprising contacting the animal tissues with a composition comprising a compound of Formula I or II at an effective amount for inhibiting tumor growth.

Yet another aspect of the present invention provides a method of inhibiting tumor progression and metastasis in animal tissues, comprising contacting the animal tissues with a composition comprising a compound of Formula I or II at an effective amount for inhibiting tumor progression and metastasis.

The present invention is broadly applicable to a variety of uses which include single agent or a component in combination therapy to treat HIF-mediated disorders or conditions with accompanying undesired angiogenesis, such as solid and blood-borne tumors including but not limited to melanomas, carcinomas, sarcomas, rhabdomyosarcoma, retinoblastoma, Ewing sarcoma, neuroblastoma, osteosarcoma, and leukemia.

Testing

Compounds of the invention have an inhibitory effect on the expression of HIF-1α and HIF-2α and on the induction of VEGF, aldolase A, and enolase 1 in cancer cells cultured under hypoxic conditions. In vivo, treatment halts the growth of xenografted tumors originating from hepatoma, stomach carcinoma, renal carcinoma, cervical carcinoma, and neuroblastoma cells. Tumors from treated mice show fewer blood vessels and reduced expression of HIF-1α and HIF-2α proteins and HIF-regulated genes than tumors from vehicle-treated mice.

The compounds induce cell cycle arrest as shown in Hep3B liver tumor cells. After application of 1 μM into cultures of Hep3B cells, typically in 48 hours, 28% of the cells were in the G0/G1 phases, 15% in the G2/M phases, 57% in the S phase, and a small percentage were characterized as being in the sub-G1 phase. In the control, typically 60% of the cells were in the G0/G1 phases, 16% in the G2/M phases, and 30% in the S-phase. This shows substantial arrest of the cell cycle such that almost double the percentage of cells are in the S-phase. This effect was dose dependent up to 5 μM for YC-1 in these cultures. Referring to FIG. 1, for YC-1 it can be seen that in plots of cell count vs. DNA content, the percentage of cells in the S-phase steadily increased with time after application.

Compounds of Formula I or II can be evaluated for efficacy using the methods described above. In addition, compounds of the invention have efficacy in in a cell viability assay using human cancer cells. The cells are treated with a compound of Formula I or II (at concentrations ranging from 0.5-2 μM) and buffer. Cellular viability is measured at 24, 48, and 72 hours. Treatment with the compound results in a notable decrease in cell viability.

Administration

The compounds of Formula I or II are administered at a therapeutically effective dosage, e.g., a dosage sufficient to provide treatment for the disease states previously described. While human dosage levels have yet to be optimized for the compounds of the invention, generally, a daily dose is from about 0.05 to 100 mg/kg of body weight, preferably about 0.10 to 10.0 mg/kg of body weight, and most preferably about 0.15 to 1.0 mg/kg of body weight. Thus, for administration to a 70 kg person, the dosage range would be about 3.5 to 7000 mg per day, preferably about 7.0 to 700.0 mg per day, and most preferably about 10.5 to 70 mg per day. The amount of active compound administered will, of course, be dependent on the subject and disease state being treated, the severity of the affliction, the manner and schedule of administration and the judgment of the prescribing physician; for example, a likely dose range for oral administration would be about 700 to 7000 mg per day, whereas for intravenous administration a likely dose range would be about 70 to 700 mg per day, the active agents being selected for longer or shorter plasma half-lives, respectively.

The nonspecific cytotoxicity of the compounds according to the invention is generally greater than 90% survival tested in vitro by MTT assay at a concentration of 5 μg/ml. In the assay cells are plated in culture plates at a density of $2 \times 10^4$ cells per well. After stabilizing for 24 hr., Hep3B cells are treated with test compound at a concentration of 5 μg/ml, then assayed after 24-hr. for viability. MTT-labeling reagent (final conc. 0.5 mg/ml) is added to each well and 4 hours later the cells are lysed with i-propyl alcohol. Absorbance is measured at 570 nm.

Administration of the compounds of the invention or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administration are customary in treating the indications that are the subject of the present invention.

Pharmaceutically acceptable compositions include solid, semi-solid, liquid and aerosol dosage forms, such as, e.g., tablets, capsules, powders, liquids, suspensions, suppositories, aerosols or the like. The compounds can also be administered in sustained or controlled release dosage forms, including depot injections, osmotic pumps, pills, transdermal (including electrotransport) patches, and the like, for prolonged and/or timed, pulsed administration at a predetermined rate. Preferably, the compositions are provided in unit dosage forms suitable for single administration of a precise dose.

The compounds can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrin derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the invention. Actual methods of preparing such dosage forms are known, or will be apparent, to those skilled in this art; for example, see *Remington's Pharmaceutical Sciences*, Mack Publishing Company, Easton, Pa.

In addition, the compounds of the invention can be co-administered with other active medicinal agents and/or administered in conjunction with other anticancer, antitumor, or anti-proliferative disease therapies. Such therapies include, but are not limited to, radiation therapy, chemotherapy, immunotherapy, laser/microwave thermotherapy, and gene therapy using antisense DNA and RNA. See Moeller et al., Cancer Cell 2004 5:429-441. Suitable additional active agents include, for example: with alfa interferons such as Interferon alfa-2b; alkylators such as asaley, AZQ, BCNU, busulfan, carboxyphthalatoplatinum, CBDCA, CCNU, CHIP, chlorambucil, chlorozotocin, clomesone, cyclodisone, cyclophosphamide, dacarbazine, dianhydrogalactitol, fluorodopan, hepsulfam, hycanthone, L-PAM, melphalan, methyl CCNU, mitomycin C, mitozolamide, nitrogen mustard, PCNU, piperazine alkylator, piperazinedione, pipobroman, porfiromycin, spirohydantoin mustard, temozolomide, teroxirone, tetraplatin, thio-tepa, triethylenemelamine, uracil nitrogen mustard, and Yoshi-864; anthracyclines such as doxorubicin, cyanomorpholinodoxorubicin, mitoxantrone, idarubicin, doxorubicin liposomal, valrubicin, epirubicin, daunomycin, and daunorubicin liposomal; antibiotics such as dactinomycin, actinomycin D, bleomycin, and daunorubicin; aromatases inhibitor such as anastrozole and letrozole; covalent conjugate of recombinant methionyl human GCSF and monomethoxypolyethylene glycol; cyclo-oxygenase inhibitors such as celecoxib; diluents such as Elliott's B Solution; enzymes such as Asparaginase; erythropoiesis stimulating proteins such as Epoetin alfa and Darbepoetin alfa; estrogen receptor modulators such as tamoxifen and fulvestrant; folate antagonists such as methotrexate; granulocyte colony stimulating factors such as Filgrastim; hormonals such as anastrozole; inorganic arsenates such as arsenic trioxide; microtubule inhibitors such as vincristine, vinblastine, paclitaxel, vinorelbine, and docetaxel; modifiers such as leucovorin and dexrazoxane; monoclonal antibodies such as anti-CD20 (Rituximab, $^{90}$Y-ibrtumomab tiuexetan, and $^{131}$-tositumomab), anti-CD22 (Epratuzumab and $^{90}$Y-epratuzumab), anti-HLA-DR (Remitogen), anti-HER2/NEU (Trastuzumab), anti-CD33 (Gemtuzumab ozogamicin), anti-CD52 (Alemtuzumab), anti-carcinoembryonic antigen ($^{90}$Y-CEA-cide), anti-epithelial cellular-adhesion molecule (Edrecolomab), anti-epidermal growth-factor receptor (Cetuximab, h-R3, and ABX-EGF), anti-VEGF (Bevacizumab), anti-VEGFR2 (IMC-1C11), anti-A33 (huA33), anti-G250/MN (G250), anti-Lewis Y antigen (SGN-15 and Hu3S193), and anti-GD3 (KW-2871); nitrosoureas such as procarbazine, lomustine, CCNU, carmustine, estramustine, and carmustine with Polifeprosan 20 Implant; nucleoside analogues such as mercaptopurine, 6-MP, fluorouracil, 5-FU, thioguanine, 6-TG, cytarabine, floxuridine (intraarterial), fludarabine, pentostatin, cladribine, pentostatin, gemcitabine, capecitabine, gemcitabine, and cytarabine liposomal; osteoclast inhibitors such as pamidronate; platinums such as carboplatin, cisplatin, and oxaliplatin; retinoids such as tretinoin, ATRA, alitretinoin, and bexarotene capsules gel; stem cell stimulators such as Oprelvekin; topoisomerase 1 inhibitors such as topotecan and irinotecan; topoisomerase 2 inhibitors such as etoposide, (VP-16), teniposide, (VM-26), and etoposide phosphate; tyrosine kinase inhibitors such as imatinib mesylate; urate-oxidase enzymes such as Rasburicase; and hydroxyurea.

In one preferred embodiment, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid that will be subsequently diluted to the above percentages. Preferably the composition will comprise 0.2-2% of the active agent in solution.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

The present invention is more specifically illustrated by the following examples. However, it should be understood that these examples are provided only for illustration of the present invention, but not intended to limit the present invention in any manner, Materials All culture media and fetal bovine serum (FBS) are purchased from Life Technologies (Grand Island, N.Y.).

EXAMPLE 1

Cell Culture

The Hep3B hepatoma was obtained from the American Type Culture Collection (Manassas, Va.). Hep3B cells were cultured in α-modified Eagle's medium. All culture media were supplemented with 10% heat-inactivated FBS, 100 units/mL penicillin, and 100 µg/mL streptomycin. All cells were grown in a humidified atmosphere containing 5% $CO_2$ at 37° C., in which the oxygen tension in the incubator (Vision Sci Co., model 9108MS2, Seoul, KOREA) was held at either 140 mm Hg (20% $O_2$, v/v, normoxic conditions) or 7 mm Hg (1% $O_2$, V/V, hypoxic conditions).

EXAMPLE 2

Effect of Compounds of Formula I or II on Hep3B Hepatoma Cell Xenografts

Male nude mice are injected subcutaneously in the flank with 5×10$^6$ viable Hep3B cells. After the tumors reached 100 to 150 mm$^3$ in size, mice receive an intraperitoneal injection of a compound of Formula I or II (30 and 10 mg/kg) or vehicle (DMSO) daily for 2 weeks. After the last treatment, the mice are euthanized, the tumors removed and analyzed.

EXAMPLE 3

In Vitro Assays for HIF-1α and HIF-2α.

Hep3B hepatoma cells are cultured in α-modified Eagle's medium supplemented with 10% heat-activated fetal bovine serum, 100 units/ml penicillin, and 100 µg/ml streptomycin in a humidified atmosphere containing 5% $CO_2$ at 37° C. Oxygen tension in the incubator is held at either 140 mm Hg (20% $O_2$, v/v, normoxia) or 7 mm Hg (1% $O_2$, v/v, hypoxia). After 24 hour stabilization under normoxic conditions, cells are incubated under normoxic or hypoxic conditions for 18 hours in the presence or in the absence of compounds of the invention. For the immunoblotting of HIF-1α or HIF-2α in cultured cells, 20 µg of extracted proteins are separated on 6.5% SDS/polyacrylamide gels, and then transferred to an Immobilon-P membrane (Millipore). Immobilized proteins are incubated overnight at 4° C. with rat anti-HIF-1α(Chun et al., J Cell Sci 2001 114:4051-4061) or anti-HIF-2α(Novus Biologicals, Littleton, Colo.), diluted 1:5000 in 5% nonfat milk in TBS/0.1% Tween-20 (TTBS). Horseradish peroxidase-conjugated anti-rat antiserum is used as a secondary antibody and the complexes are visualized using an Enhanced Chemiluminescence Plus Kit (Amersham Pharmacia Biotec). Among the analogs with observed inhibition activity, {5-[1H-benzimidazol-1-yl]-furan-2-yl}-methanol and {5-[1-(prop-2-yl)-1H-indazol-3-yl]-furan-2-yl}-methanol are strong inhibitors of HIF-1α and HIF-2α

EXAMPLE 4

Effects on Angiogenesis, HIF-1α Protein, and VEGF Expression

To determine the mechanism by which the compounds of the invention inhibit tumor growth, Hep3B tumors were examined morphologically and biochemically. Male nude mice were injected subcutaneously in the flank with 5×10$^6$ viable Hep3B cells. After the tumors reached 100 to 150 mm³ in size, mice received an intraperitoneal injection of the test compound (30 and 10 mg/kg) or vehicle (DMSO) daily for 2 weeks. After the last treatment, the mice were euthanized, the tumors, removed, fixed with formalin, and embedded in paraffin. Serial sections (6 μm thick) were cut from each paraffin block. One section was stained with hematoxylin and eosin (H&E) for histological assessment. Hematoxylin-eosin stained tumor sections from vehicle-treated mice revealed well-developed blood vessels containing red blood cells and frequent mitotic figures. By contrast, hematoxylin-eosin stained tumor sections treated mice tumors revealed frequent acinus formation without well-developed blood vessels.

To determine whether the inhibitory effect on tumor growth is associated with the suppression of tumor angiogenesis, we examined the distribution of the endothelial marker, CD31. Other sections were immunochemically stained for HIF-1α and the endothelial cell marker CD31. First, the sections were deparaffinized and rehydrated through a graded alcohol series. Next, the sections were heated in 10 mM sodium citrate (pH 6.0) for 5 min in a microwave to retrieve the antigens. After blocking nonspecific sites with a blocking solution containing 2.5% BSA (SigmaAldrich Corp., St. Louis, Mo.) and 2% normal goat serum (Life Technologies) in a phosphate-buffered saline (pH 7.4) for 1 h, the sections were incubated overnight at 4° C. with rabbit polyclonal anti-CD31 (SantaCruz, 1:100 dilution in the blocking solution) or rat anti-HIF-1α (1:100 dilution in the blocking solution) antibodies, as described previously (Kim et al., Circ Res 2002 90:E25-E33). Negative control sections were incubated with diluent in the absence of any primary antibodies. The sections were then stained using standard methods, and the avidin-biotin-horseradish peroxidase complex was used to localize the bound antibodies, with diaminobenzidine as the final chromogen. All immunostained sections were lightly counterstained with hematoxylin. Few CD31-immunopositive vessels were observed in tumor sections from drug-treated mice, whereas many vessels were observed in tumor sections from vehicle-treated mice.

EXAMPLE 5

Preparation of
[5-(benzimidazol-1-yl)-furan-2-yl]-methanol

Benzimidazole is mixed with 5-bromo-furan-2-yl formaldehyde in the presence of CuI/N,N'-dimethylethylenediamine and cesium carbonate. The resulting [5-(benzimidazol-1-yl)-furan-2-yl]-formaldehyde is purified, then reduced to the title compound with sodium borohydride.

EXAMPLE 6

The percentage of viable cells was measured by MTT assay. Cells were plated in 12 well plates. After incubating cells for indicated time with DMSO or YC-1, MTT was add to media, final concentration of 0.5 mg/ml, and incubated for 3 h at 37° C. Resulting insoluble formazan was dissolved with 0.04 N HCl in isopropanol. Absorbance of purple color of formazan was measured at 570 nm with a spectrophotometer. Cells were incubated with 0.5, 1, or 2 μM YC-1 for 24, 48, or 72 h. Cell viability was decreased by YC-1, dose-dependently and time-dependently (FIG. 2).

EXAMPLE 7

Figure 3A:
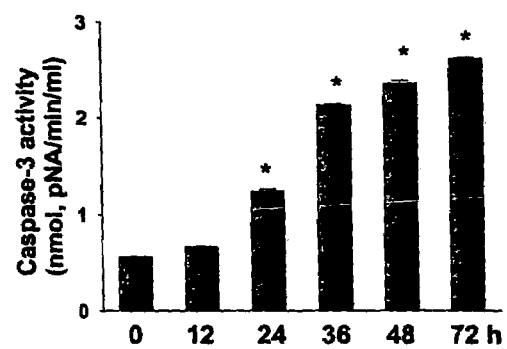
FIG. 3a shows caspase-3 activity. The activity of caspase-3 in Hep3B cell extracts that had been treated with vehicle or 1 µM YC-1 for indicated time was measured by using a caspase-3 activity assay kit. The activity of caspase-3 was represented in nmoles of p-nitroaniline released per min and per ml of cellular extract. Bars represent the mean of three separate experiments with the upper 95% confidence interval. *: $p<0.05$ vs. the control.
Figure 3B:
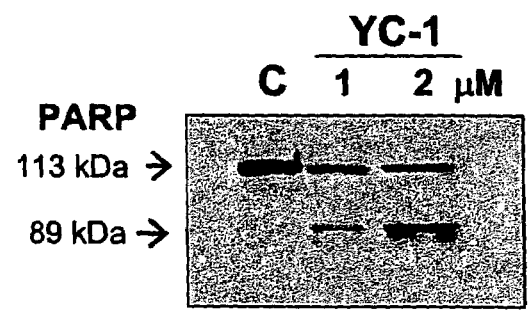
FIG. 3b shows PARP-cleavage. Hep3B cells were treated with 1, 2 µM YC-1 for 90 h. PARP cleavage was analysed by immunoblotting with a mouse anti-PARP antibody. Proteins were visualized by Enhanced Chemiluminescence Plus. The lane C is the control.
Figure 3C:
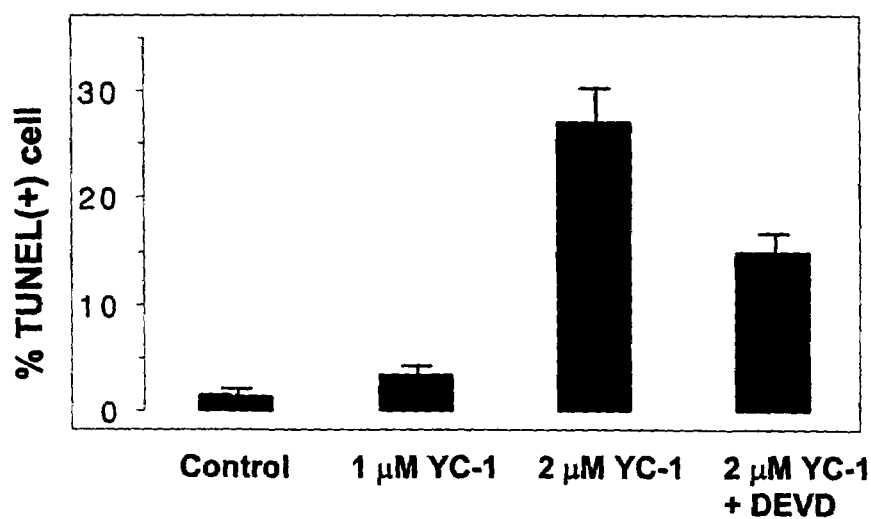
FIG. 3c shows the TUNEL assay. For quantification of apoptosis at single cell level, based on labeling of DNA strand breaks, Hep3B cells were treated with 1, 2 μM YC-1 for 90 h, and Ac-DEVD-CHO, Caspase-3 inhibitor was treated before 1 h prior to treat YC-1.
Figure 4A:
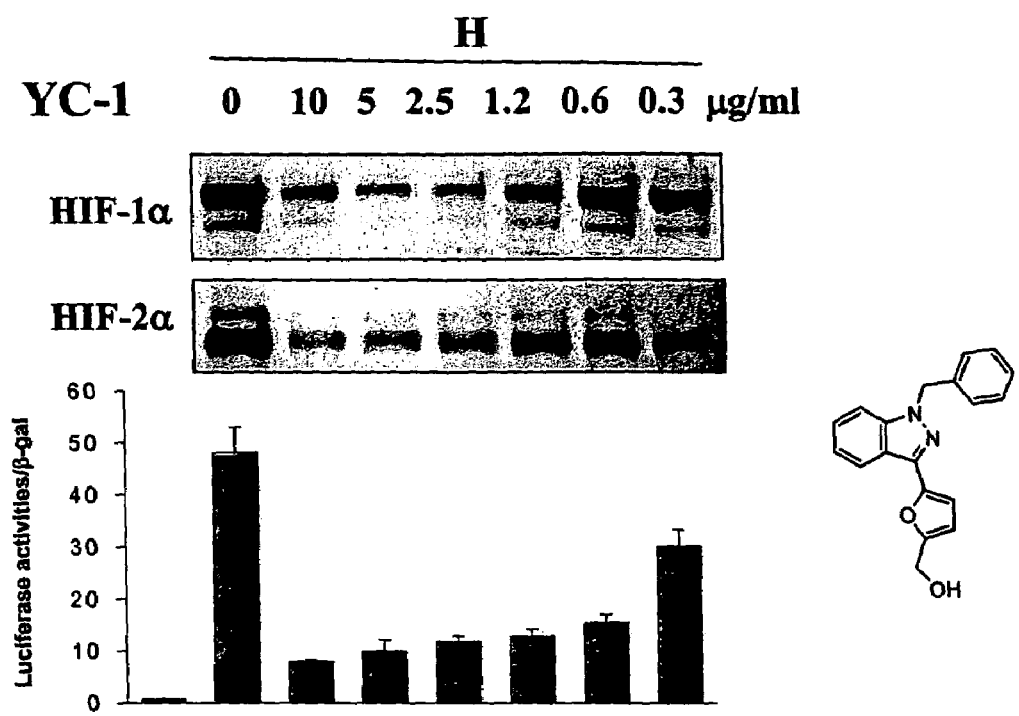
FIGS. 4a through 4i show the protein amounts of HIF-1α and HIF-2α, and the transcriptional activities of HIF (reporter assay). These indicate both the protein suppression and transcriptional inhibition of HIF by various compounds of the invention under hypoxic conditions.
Figure 4B:
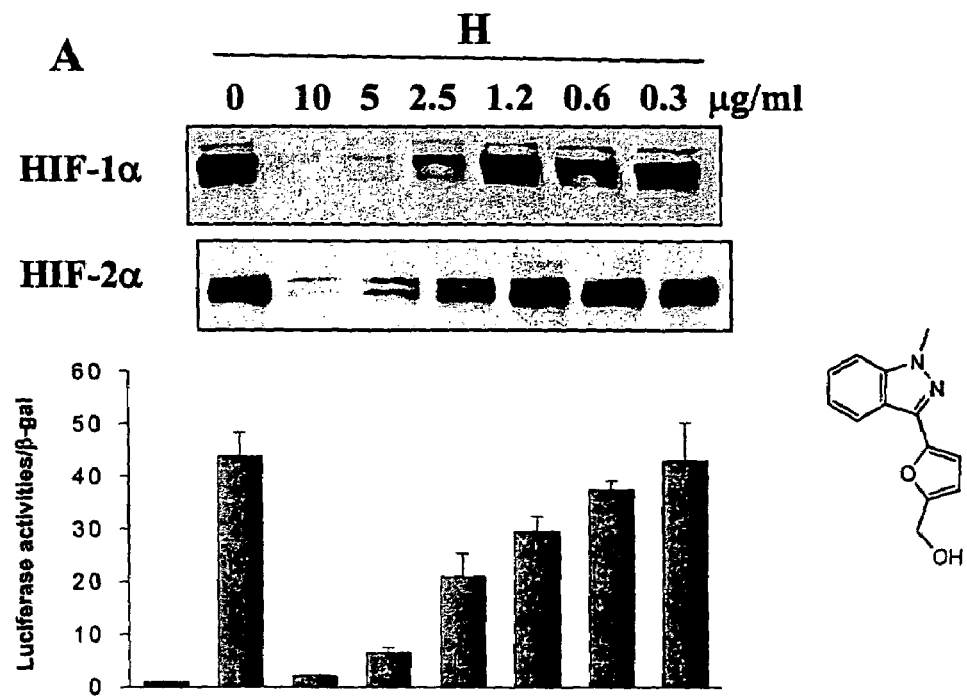
Figure 4C:
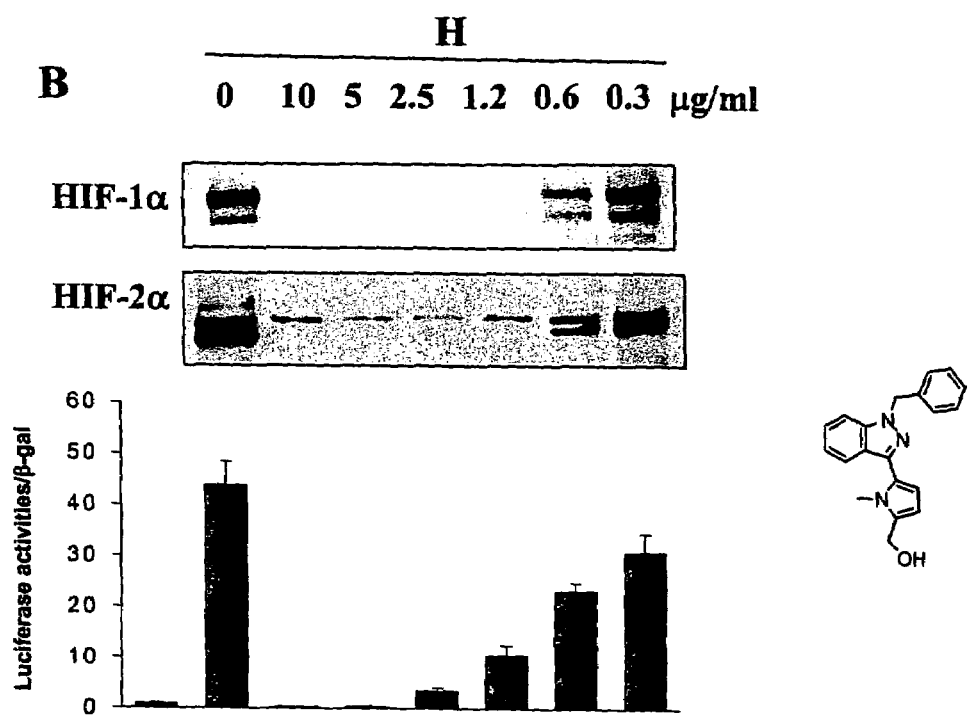
Figure 4D:
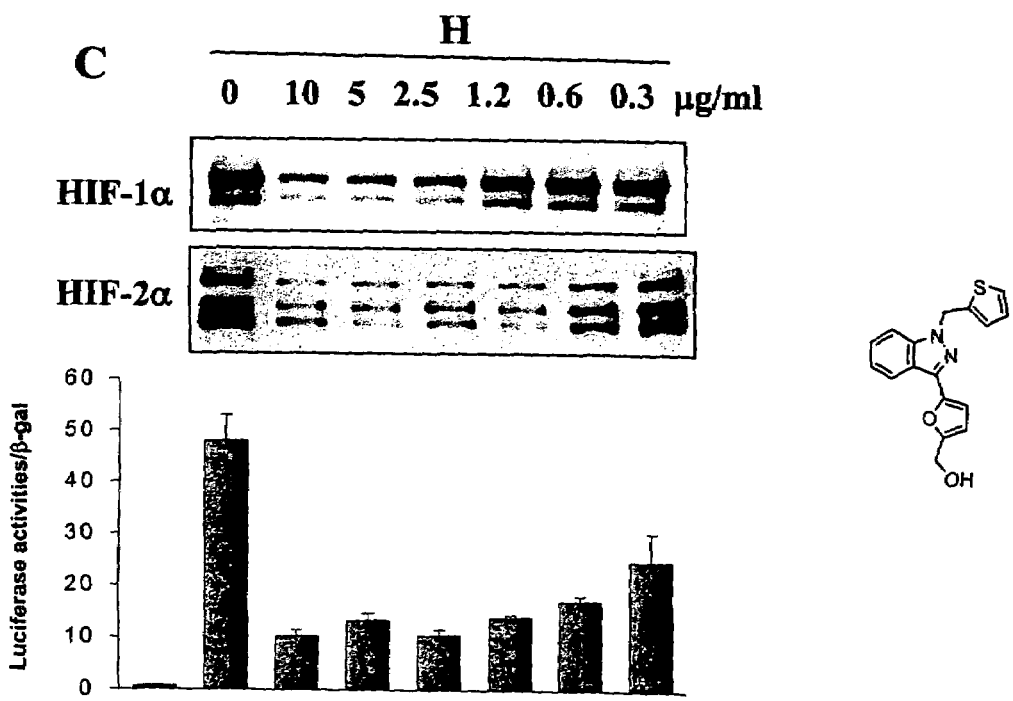
Figure 4E:
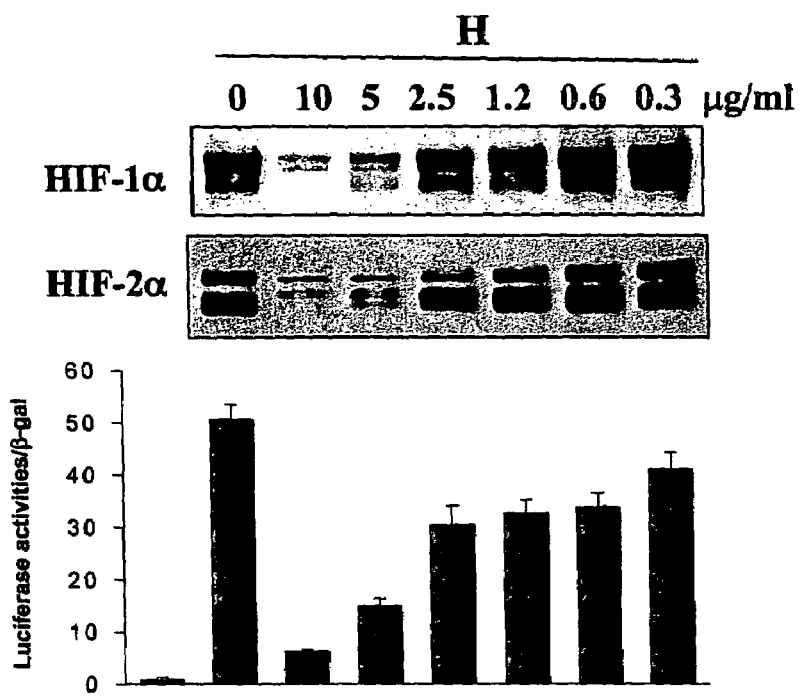
Figure 4F:
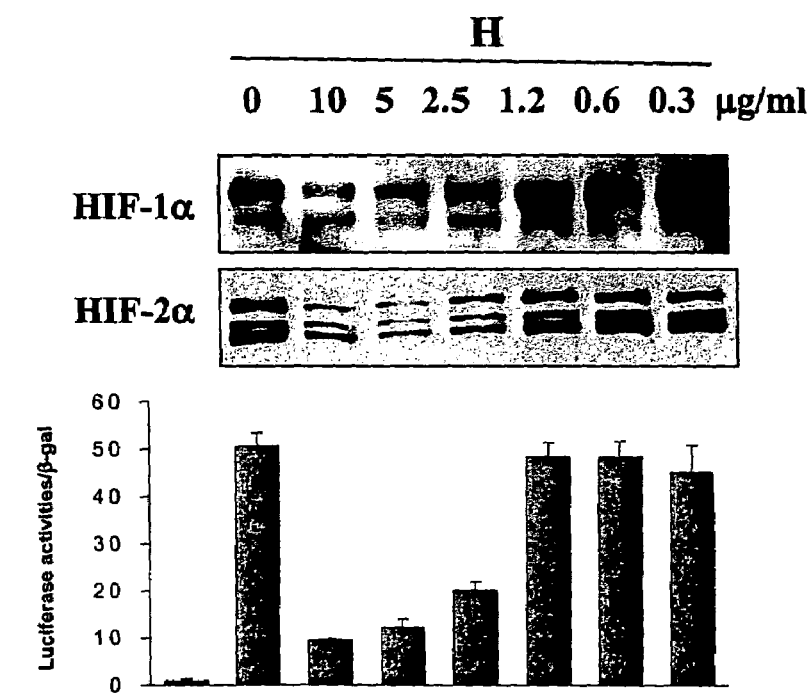
Figure 4G:
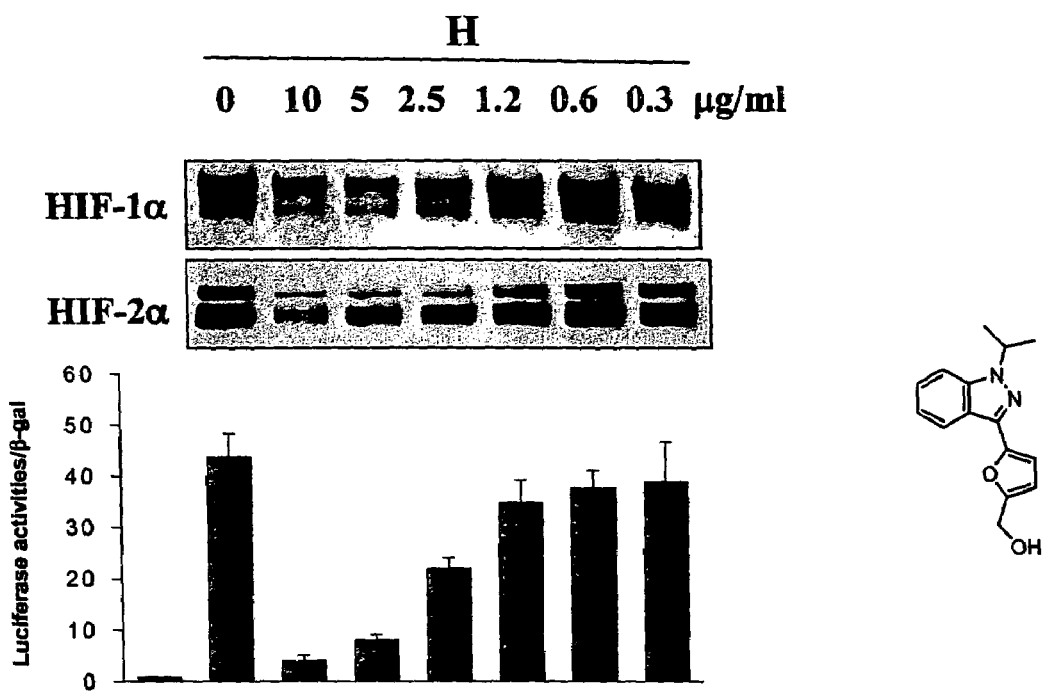
Figure 4H:
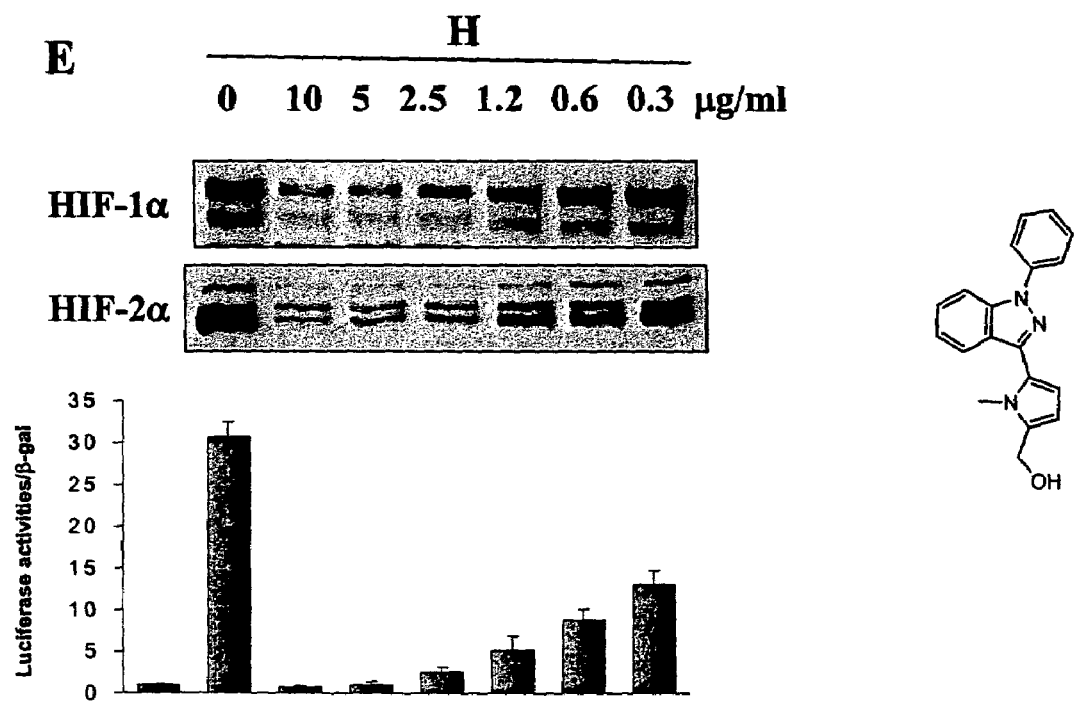
Figure 4I:
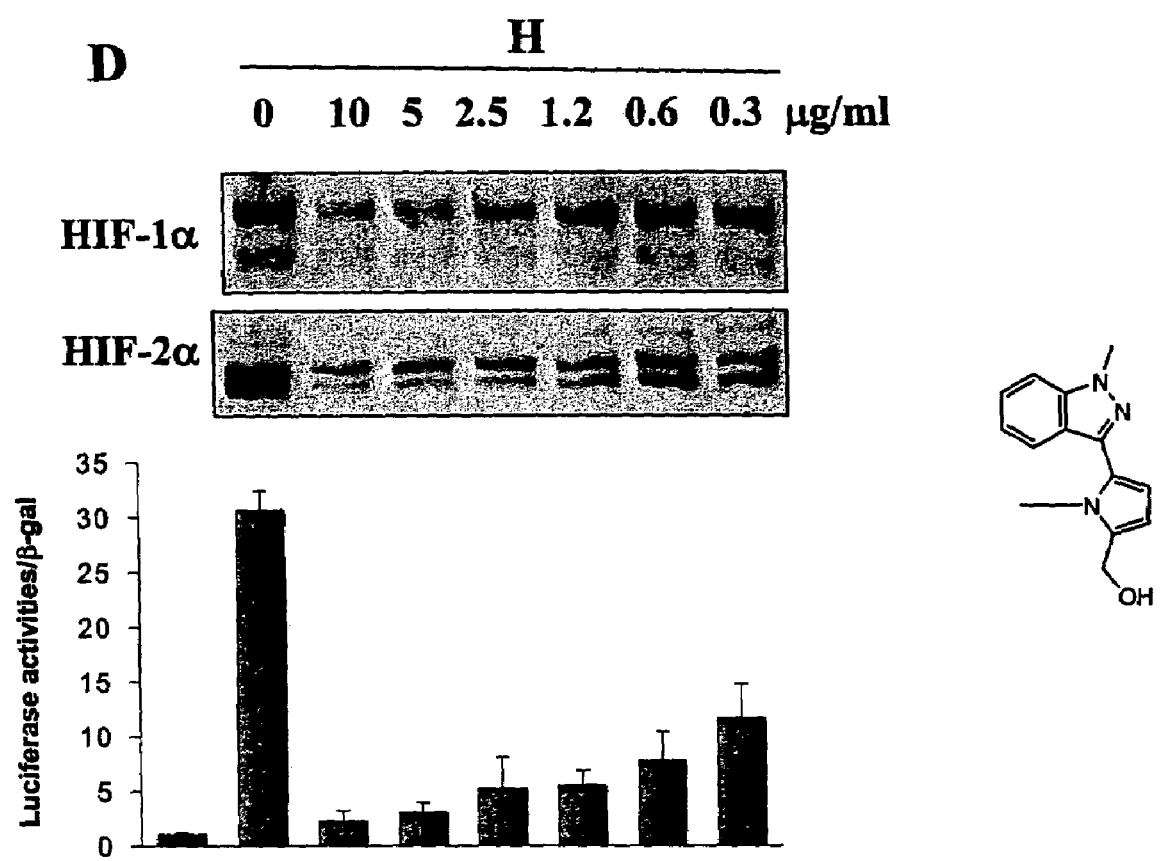
Figures 5A, 5B:
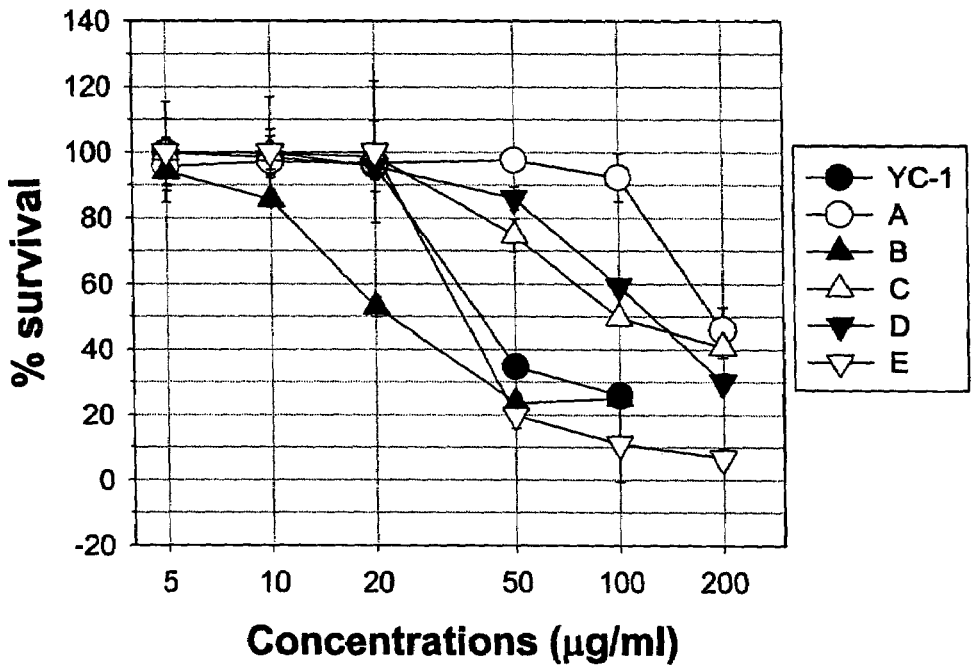
FIGS. 5a and 5b represent, respectively, the data on toxicity in vitro and acute toxicity in vivo of four compounds of the invention. YC-1 is also shown for comparison.
Figure 6A:
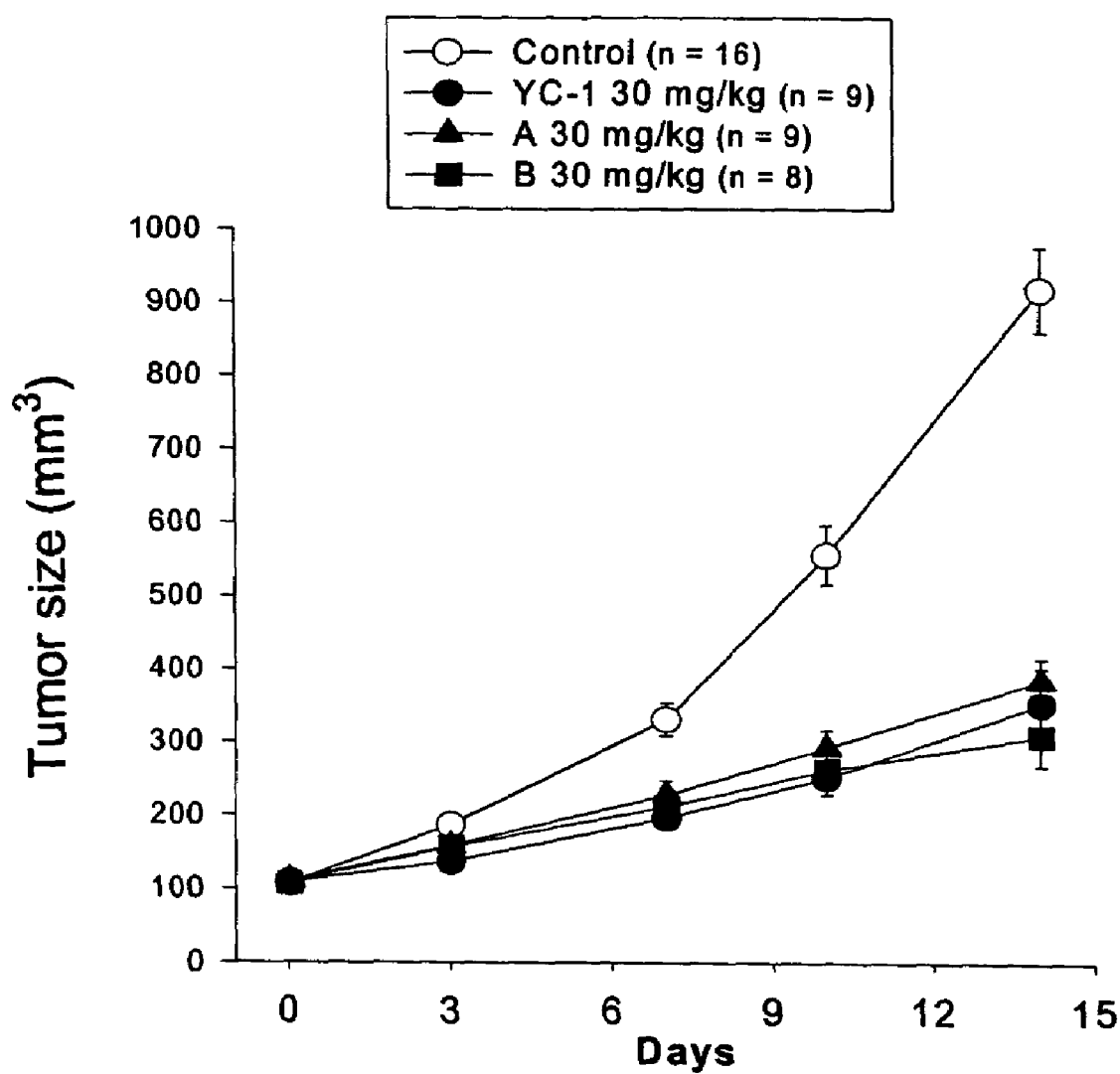
FIGS. 6a and 6b are plots of the tumor growth inhibition in vivo at, respectively, dosages of 30 mg/kg and 10 mg/kg for two compounds of the invention. An untreated control and YC-1 are shown for comparison.
Figure 6B:
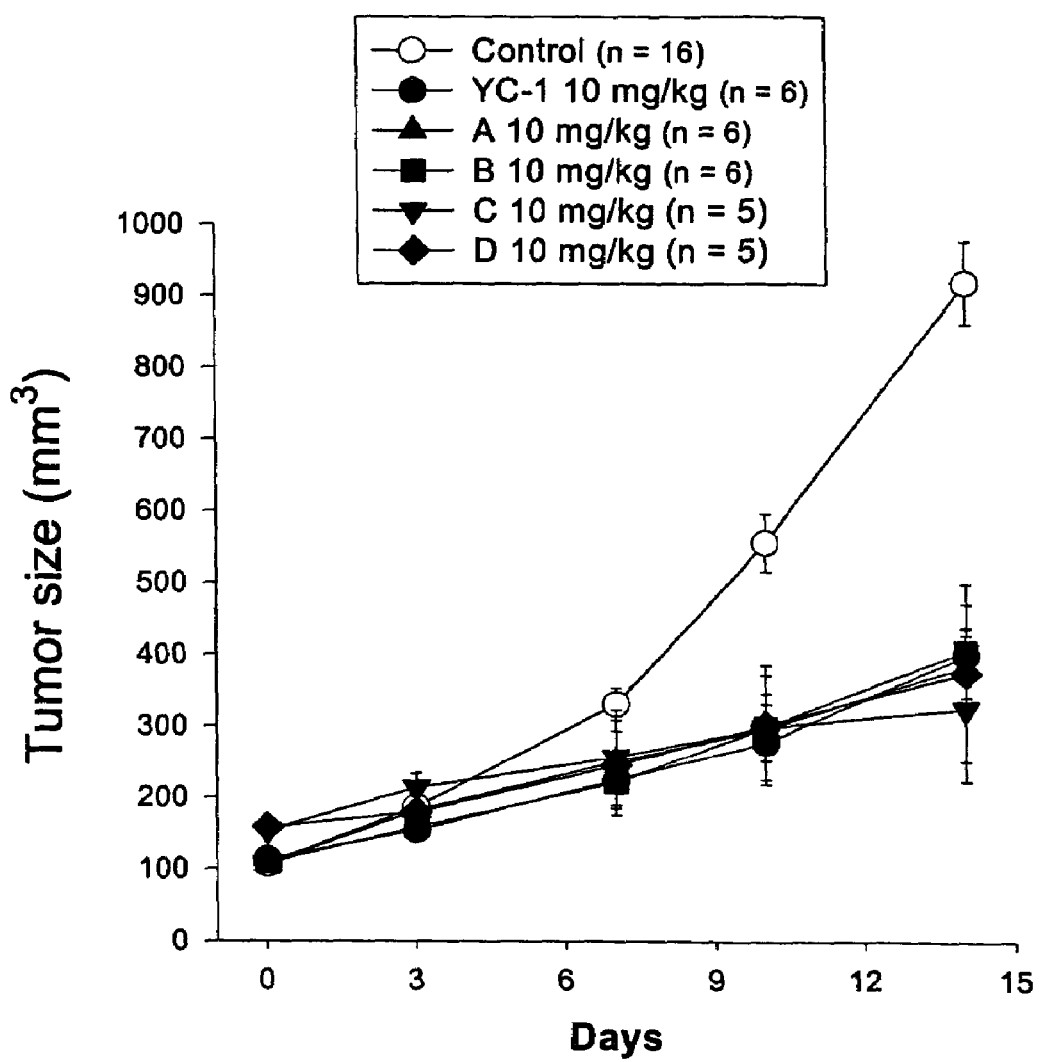

To test the effect of YC-1 on apoptosis, YC-1 (1 μM) was introduced to a culture of Hep3B and the caspase-3 activity was monitored for 72 h. Referring to FIG. 3a, the caspase-3 activity increased over time to about 5 times the activity in the control after 72 h. Caspase-3 is an enzyme that cleaves the 113 kDa protein poly-ADP-ribose-polymerase (PARP) to form an inactive 89 kDa fragment. Inactivation of PARP leads to cell apoptosis. PARP protein was analyzed using Western blotting with anti-PARP antibody (BIOMOL Research Laboratories, Inc), diluted 1:5000. Referring to FIG. 3b, the amount of the 89 kDa fragment of PARP increased when the YC-1 dose was doubled, without apparent effect on actin production. For quantification of apoptosis at single cell level, based on labeling of DNA strand breaks, Terminal deoxynucleotidyl Transferase-mediated dUTP Nick End Labeling (TUNEL) assay was performed according to the manufacturer's protocol (In Situ Cell Death Detection Kit; TMR Red; Roche Diagnostics GmbH, Mannheim, Germany). It is a method for detecting the 3'—OH ends of DNA exposed during the internucleosomal cleavage that occurs during apoptosis. Incorporation of fluorescein-dUTP allows detection by FACS. Cell were harvested, fixed directly with final 2% PFA for 1 h at room temperature and permeabilized with 0.1% Triton X-100 in 0.1% sodium citrate for 5 mm on ice. After labeling with TUNEL reaction mixture with TdT for 1 h at 37 0C, staining with propidium iodide following FACS analysis. Referring to FIG. 3c, the percentage of TUNEL-positive cells increased dose-dependently. When caspase-3 inhibitor was pre-treated before 1 h prior to treat YC-1, the percentage of TUNEL-positive cells decreased significantly.

EXAMPLE 8

Measurement of HIF Proteins

To induce HIF-1α and HIF-2α proteins, Hep3B cells were incubated in a hypoxic chamber (1% oxygen tension) for 16 hours. YC-1 and related compound at various concentrations (0.3 to 10 μg/ml) were administered into the culture media just before hypoxic incubation. The amounts of HIF proteins were measured by Western blotting method. Referring to FIGS. 4a through FIG. 4i, YC-1 and related compounds effectively reduced the expressions of HIF proteins.

HIF Activity Assay

The synthetic DNA coding the HIF-binding enhancer region of the EPO gene, 5-GGTACCGGCCCTACGTGCT-GTCTCACACAGCCTGTCTGACCTCTC-
GACCTACCGGCCAG ATCT-3 (SEQ. ID NO. 1), was inserted into the pGL3 promoter plasmid (Promega). To assay the HIF activity, Hep3B cells were cotransfected with the luciferase reporter gene and the plasmid cytomegalovirus-β-gal, using the calcium phosphate method. Transfected cells were split into nine aliquots and incubated for 42 h. After stabilizing, the cells were incubated for 16 h at 20% or 1% O₂. They were then lysed and assayed for luciferase activity using a Biocounter M1500 luminometer (Lumac).

β-gal assays were performed for normalization of transfection. Referring to FIGS. 4a through FIG. 4i, YC-1 and related compounds effectively reduced HIF activity.

EXAMPLE 9

[5-(1-Methyl-1H-indazol-3-yl)-furan-2-yl]-methanol (Compound A)

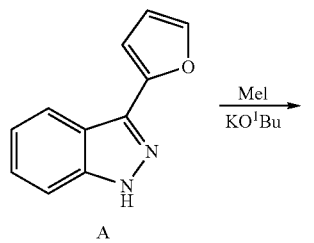

A

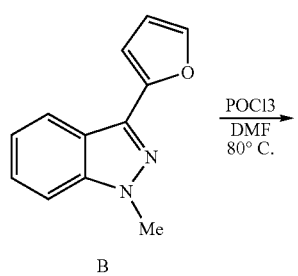

B

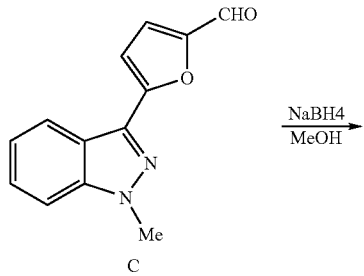

C

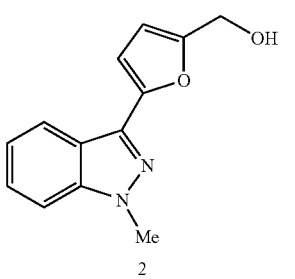

2

N-Methylfuranylindazole B was prepared from furanylindazole A and iodomethane in the presence of potassium t-butoxide at room temperature. Vilsmier-Haack reaction (POCl₃/DMF) of furanylindazole B gave the corresponding aldehyde D which was then subjected to NaBH₄ reduction to give the title compound 2.

EXAMPLE 10

[1-Benzyl-5-(1-methyl-1H-indazol-3-yl)-1H-pyrrol-2-yl]-methanol (Compound B)

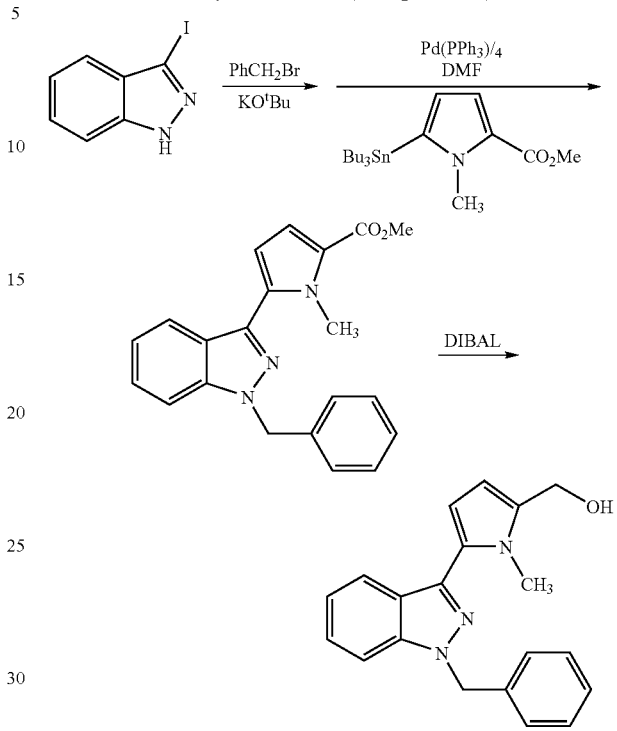

EXAMPLE 11

[1-Methyl-5-(1-methyl-1H-indazol-3-yl)-1H-pyrrol-2-yl]-methanol (Compound D)

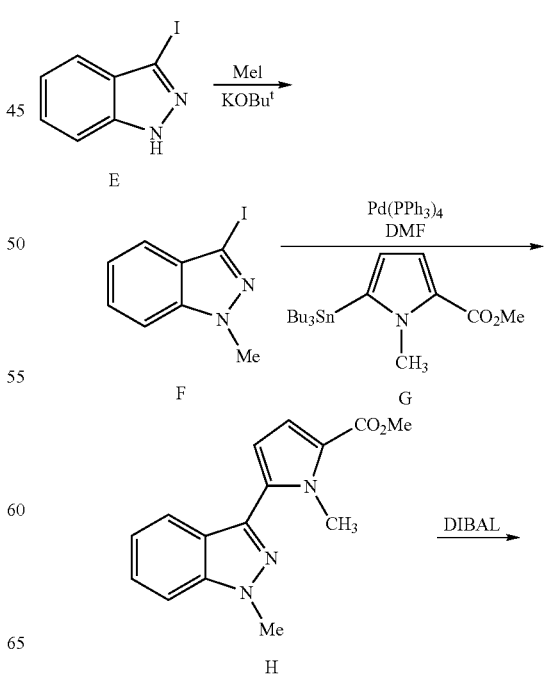

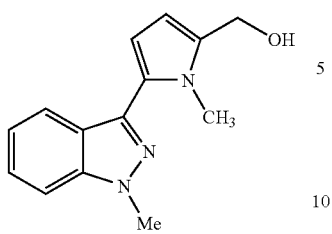

Methylation of iodoindazole E (iodomethane/potassium t-butoxide) was followed by Stille coupling of resulting N-methyliodoindazole F with tin compound G in the presence of catalytic Pd(0) to give the desired methyl ester H. Dibal reduction of methyl ester at 0° C. gave the title compound.

EXAMPLE 12

[5-(1-Thiophen-2-yl-methyl-1H-indazole-3-yl)-furan-2-yl]-methanol (Compound C)

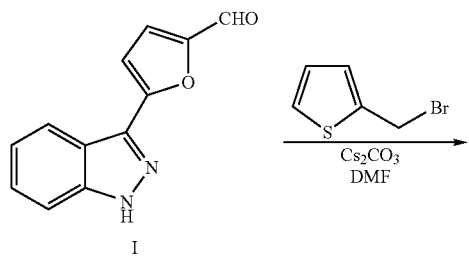

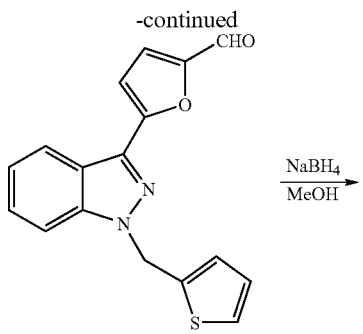

Reaction of furan-carboxaldehyde I with 2-bromomethylthiophene in the presence of cesium carbonate as a base gave the desired product J and the 2-position alkylated regio-isomer. The desired isomer J was purified by careful silica gel column chromatography and then subjected to a NaBH$_4$ reduction to give the title compound.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All patents and publications cited above are hereby incorporated by reference.

---

The invention claimed is:
1. The compound [5-(1-methyl-1H-indazol-3-yl)-furan-2-yl]-methanol.
2. A pharmaceutical composition comprising the compound according to claim 1, and a pharmaceutically acceptable carrier thereof.

* * * * *

SEQUENCE LISTING

<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: HIF-binding enhancer region of EPO gene

<400> SEQUENCE: 1

```
ggtaccggcc ctacgtgctg tctcacacag cctgtctgac ctctcgacct accggccaga    60
tct                                                                  63
```